(12) United States Patent
Stone

(10) Patent No.: US 11,191,451 B2
(45) Date of Patent: Dec. 7, 2021

(54) WEARABLE MONITORING SYSTEM AND METHODS FOR DETERMINING RESPIRATORY AND SLEEP DISORDERS WITH SAME

(71) Applicant: Medical Design Solutions, Inc., Milpitas, CA (US)

(72) Inventor: Robert T Stone, Sunnyvale, CA (US)

(73) Assignee: Medical Design Solutions, Inc., Milpitas, CA (US)

( * ) Notice: Subject to any disclaimer, the term of this patent is extended or adjusted under 35 U.S.C. 154(b) by 223 days.

(21) Appl. No.: 16/363,290

(22) Filed: Mar. 25, 2019

(65) Prior Publication Data

US 2019/0216364 A1 Jul. 18, 2019

Related U.S. Application Data

(63) Continuation-in-part of application No. 16/117,921, filed on Aug. 30, 2018, now Pat. No. 10,314,517, which is a continuation of application No. 15/133,497, filed on Apr. 20, 2016, now Pat. No. 10,064,570, which is a continuation-in-part of application No. 13/854,280, filed on Apr. 1, 2013, now abandoned.

(51) Int. Cl.
| | |
|---|---|
| *A61B 5/08* | (2006.01) |
| *A61B 5/091* | (2006.01) |
| *A61B 5/00* | (2006.01) |
| *A61B 5/01* | (2006.01) |
| *A61B 5/113* | (2006.01) |
| *A61B 5/0205* | (2006.01) |

(52) U.S. Cl.
CPC .............. *A61B 5/091* (2013.01); *A61B 5/01* (2013.01); *A61B 5/08* (2013.01); *A61B 5/1135* (2013.01); *A61B 5/4818* (2013.01); *A61B 5/6804* (2013.01); *A61B 5/6805* (2013.01); *A61B 5/6831* (2013.01); *A61B 5/7257* (2013.01); *A61B 5/742* (2013.01); *A61B 5/02055* (2013.01); *A61B 2562/0223* (2013.01)

(58) Field of Classification Search
None
See application file for complete search history.

(56) References Cited

U.S. PATENT DOCUMENTS

| | | |
|---|---|---|
| 8,790,273 B2 | 7/2014 | McCool |
| 8,790,274 B2 | 7/2014 | McCool |
| 9,414,771 B2 | 8/2016 | McCool |
| 2004/0122334 A1 | 6/2004 | Yamashiro |

(Continued)

FOREIGN PATENT DOCUMENTS

| | | |
|---|---|---|
| GB | 2176610 A | 12/1986 |
| WO | WO-2017/184129 A1 | 10/2017 |

*Primary Examiner* — Eric J Messersmith
(74) *Attorney, Agent, or Firm* — Francis Law Group

(57) ABSTRACT

A wearable monitoring system and associated method that is configured to (i) determine three dimensional displacement of the spine of a subject's chest wall with respect to the subject's spine, (ii) process the three dimensional anatomical data, (iii) determine at least one respiratory parameter associated with the monitored subject and value thereof as a function of the three dimensional anatomical data, and (iv) determine a respiratory disorder as a function of the determined respiratory parameter and value thereof.

27 Claims, 5 Drawing Sheets

(56) References Cited

U.S. PATENT DOCUMENTS

| | | |
|---|---|---|
| 2008/0255468 A1 | 10/2008 | Derchak et al. |
| 2011/0054271 A1* | 3/2011 | Derchak ................ G16H 40/63 600/301 |
| 2014/0296651 A1 | 10/2014 | Stone |
| 2015/0073717 A1 | 3/2015 | Hsu |
| 2016/0192856 A1* | 7/2016 | Lee ..................... A61B 5/0006 600/384 |
| 2018/0184735 A1 | 7/2018 | Longinotti-Buitoni et al. |

* cited by examiner

WEARABLE MONITORING SYSTEM AND METHODS FOR DETERMINING RESPIRATORY AND SLEEP DISORDERS WITH SAME

CROSS-REFERENCES TO RELATED APPLICATIONS

This application is continuation-in-part of U.S. application Ser. No. 16/117,921, filed on Aug. 30, 2018, which is a continuation of U.S. application Ser. No. 15/133,497, filed on Apr. 20, 2016, now U.S. Pat. No. 10,064,570, which is a continuation-in-part of U.S. application Ser. No. 13/854,280, filed on Apr. 1, 2013.

FIELD OF THE INVENTION

The present invention relates to systems and methods for monitoring physiological characteristics of a subject. More particularly, the present invention relates to apparatus, systems and methods for determining a plurality of respiratory characteristics, and respiratory and sleep disorders exhibited thereby.

BACKGROUND OF THE INVENTION

It has been estimated that approximately 10% of adults are affected by a respiratory disorder. Most respiratory disorders are deemed a serious risk factor because they can, and often will, have a long-term effect on the cardiovascular system. Indeed, sympathetic modulation has been found to be closely related to adverse heart rate variability, e.g., cardiac arrhythmia.

The most common respiratory disorders that affect adults are apneas, i.e. sleep apneas and hypopnea.

As is well known in the art, sleep apnea is generally classified into three types based on respiratory functions. The first type of apnea is obstructive sleep apnea (OSA), which occurs when the subject or patient stops breathing continuously due to an obstructed upper airway.

The second type of apnea is central sleep apnea (CEN), which occurs when the subject or patient stops breathing continuously due to the inability of the subject to correctly modulate respiration, i.e. the brain temporarily fails to transmit appropriate neurological signals to the muscles responsible for controlling breathing. Unlike obstructive sleep apnea, which can be thought of as a mechanical problem, central sleep apnea is more of a communication problem.

The third type of apnea is generally referred to as mixed apnea, which is a combination of obstructive and central sleep apnea. Mixed apnea is generally characterized by a lack of respiratory effort without air exchange due to upper airway obstruction.

Hypopnea is a respiratory disorder that is characterized by overly shallow breathing or an abnormally low respiratory rate (f), i.e. a decreased amount of air movement into the lungs, which can, and often will cause oxygen levels in the blood to drop.

As is also well known in the art, various abnormal seminal respiratory parameters and/or characteristics, such as breathing frequency (e.g. breaths per minute), tidal volume ($V_T$), inspiration volume, expiration volume, respiratory minute ventilation (e.g. inspiration volume per minute or expiration volume per minute) and/or peak expiratory flow rate, and physiological parameters and/or characteristics, such as oxy-hemoglobin saturation and oxygen desaturation index, are indicative of a sleep apnea and/or hypopnea.

Various systems and methods have thus been developed to detect one or more respiratory parameters and determine a respiratory disorder, such as sleep apnea, therefrom. Most of the systems and methods are based on anatomical displacements and the relationships thereof to one or more of the above referenced respiratory parameters and characteristics, e.g., breathing frequency, $V_T$ and inspiration volume.

Illustrative are the systems and methods for determining respiratory parameters disclosed in U.S. Pat. Nos. 8,790,273 and 8,790,274 (hereinafter "McCool patents"). The systems disclosed in the referenced McCool patents generally comprise at least two tuned pairs of electromagnetic (EM) coils (also referred to herein as "magnetometers"), where each pair of EM coils comprise a single-channel transmitter EM coil that is adapted to transmit a specific high-frequency AC electromagnetic field (i.e. transducer) and an EM coil (i.e. receiver) that is adapted to receive the AC electromagnetic field transmitted by the transmitter EM coil.

The transmitter EM coil(s) of the McCool systems are positioned on the front of a subject and the receiver EM coils are positioned on the back of the subject.

The systems disclosed in the McCool patents are configured to determine at least one respiratory parameter or characteristic; particularly, tidal volume ($V_T$) as a function of a plurality of anatomical distances, e.g., rib cage-anteroposterior distance and abdomen-anteroposterior distance, which are detected by the tuned pairs of EM coils, and a plurality of predetermined volume-motion coefficients.

A major drawback and disadvantage associated with the McCool systems and associated methods is the use of single-channel transmitter EM coils that (i) are limited to one (1) specific AC electromagnetic field frequency and (ii) are susceptible to interference from extraneous electromagnetic fields that negatively impact the voltage output of the EM coils and, hence, the consistency of the AC electromagnetic field frequency.

A further drawback and disadvantage associated with the McCool systems is that the McCool systems and associated methods are dependent on the use of complex algorithms, which can, and often will, fail to quantitatively account for physiological differences between individual subjects. As a result, the McCool systems are incapable of consistently providing accurate determinations of seminal physiological parameters and/or characteristics, such as tidal volume ($V_T$) and minute ventilation (V-dot).

Another drawback and disadvantage associated with the McCool systems is the extensive amount of cumbersome wiring that is required for the McCool systems to operate.

Further systems and methods for determining respiratory parameters and respiratory disorders associated therewith are disclosed in Applicant's issued U.S. Pat. No. 10,064,570 and Co-pending U.S. application Ser. No. 16/117,921.

In contrast to the McCool systems, the systems disclosed in U.S. Pat. No. 10,064,570 and Co-pending U.S. application Ser. No. 16/117,921 comprise at least one permanent magnet coupled with at least one magnetometer that is configured to receive the AC electromagnetic field generated by the permanent magnet. The magnetometer is positioned on the front of a subject proximate the xyphoid process and the permanent magnet is positioned on the back of the subject proximate the spine and across from the xyphoid process of the subject.

The magnetometer of the above noted systems is adapted to detect strength variations in the AC magnetic field emitted by the permanent magnet, which reflect displacements, i.e.

change in distance, by and between the magnetometer and permanent magnet and, hence, anatomical displacements of the subject. The systems are then programmed and configured to determine at least one respiratory parameter of the subject as a function of the anatomical displacements of the subject.

A seminal advantage of the systems disclosed in U.S. Pat. No. 10,064,570 and Co-pending U.S. application Ser. No. 16/117,921 comprises the use of a permanent rare earth magnet that is capable of generating an AC magnetic field with a substantially higher degree of magnetic field strength per unit mass compared to conventional magnetic field transducers.

Further advantages provided by the permanent rare earth magnet are that the permanent magnet is capable of providing an AC magnetic field with (i) a greater degree of magnetic field stability over time compared to conventional magnetic field transducers and (ii) that is minimally impacted by interference from extraneous electromagnetic fields compared to conventional magnetic field transducers. The systems disclosed in U.S. Pat. No. 10,064,570 and Co-pending U.S. application Ser. No. 16/117,921 are thus capable of measuring multiple respiratory parameters associated with a user or wearer with a high degree of accuracy, while minimizing inference from external sources, such as electromagnetic radiation.

Further, since permanent rare earth magnets do not require an external power source or control module to generate an AC magnetic field, the systems disclosed in U.S. Pat. No. 10,064,570 and Co-pending U.S. application Ser. No. 16/117,921 require substantially less wiring and electrical power to operate compared to conventional systems, such as the systems disclosed by McCool.

Although the systems disclosed in U.S. Pat. No. 10,064,570 and Co-pending U.S. application Ser. No. 16/117,921 can be readily employed to accurately determine multiple respiratory parameters in real time and determine respiratory disorders; particularly, apneas and hypopnea therefrom, it is desirable to provide an improved system based thereon with enhanced respiratory and physiological parameter detection accuracy and, thereby, respiratory disorder determination.

It is therefore an object of the present invention to provide an improved respiratory monitoring system that accurately detects and measures respiratory parameters and/or characteristics in real time based on anatomical displacements of a monitored subject.

It is another object of the present invention to provide a respiratory-physiological parameter monitoring system that accurately detects and measures respiratory and physiological parameters and characteristics in real time based on anatomic displacements of a monitored subject.

It is another object of the present invention to provide improved methods for determining a respiratory disorder based on detected respiratory and/or physiological parameters and/or characteristics.

It is another object of the present invention to provide improved methods for determining sleep disorder, including sleep apnea and/or hypopnea, based on detected abnormal respiratory and/or physiological parameters and/or characteristics.

SUMMARY OF THE INVENTION

The present invention is directed to respiratory parameter and respiratory-physiological parameter monitoring systems and improved methods using same for determining respiratory and/or sleep disorders based on anatomical displacements and measured physiological parameters and/or characteristics.

In a preferred embodiment of the invention, the respiratory parameter and respiratory-physiological parameter monitoring systems comprise a wearable garment that is configured to cover at least the chest region and upper back of a subject (or user).

In a preferred embodiment of the invention, the respiratory parameter monitoring system comprises a respiratory parameter monitoring sub-system, an electronics control-processing module, and integral signal transmission means associated therewith.

In a preferred embodiment of the invention, the respiratory-physiological parameter monitoring system further comprises a physiological parameter monitoring sub-system.

In a preferred embodiment of the invention, the respiratory parameter monitoring sub-system comprises at least one permanent magnet and at least one electromagnetic coil or magnetometer, which is configured and positioned to detect and measure magnetic field strengths in at least one field dimension of the AC magnetic field generated by the permanent magnet, and generate AC magnetic field strength signals representing the magnetic field strengths in the AC magnetic field dimension and, thereby, anatomical displacement of the monitored subject.

In some embodiments of the invention, the respiratory parameter monitoring sub-system comprises at least one permanent magnet and a plurality of magnetometers, which are configured and positioned to detect and measure magnetic field strengths in the AC magnetic field dimensions generated by the permanent magnet, and generate a plurality of AC magnetic field strength signals representing the magnetic field strengths in the AC magnetic field dimensions and, thereby, anatomical displacements of the monitored subject.

In a preferred embodiment of the invention, the physiological parameter monitoring sub-system comprises at least one physiological parameter sensor that is configured to detect and measure a physiological parameter and, preferably, a value thereof, and generate and transmit a physiological parameter signal representing the measured physiological parameter.

In some embodiments, the physiological parameter monitoring sensor comprises a $SpO_2$ sensor that is configured to monitor $SpO_2$ of a monitored subject and generate and transmit $SpO_2$ signals representing same.

In some embodiments of the invention, the physiological parameter monitoring sub-system further comprises an accelerometer that is configured and positioned to establish orientations of the subject and monitor physical movement of the subject.

In a preferred embodiment of the invention, the electronics module, i.e. electronics control-processing module, is programmed and configured (i.e. comprises programs, parameters, instructions and at least one algorithm) to control the respiratory parameter and respiratory-physiological parameter monitoring systems and the function thereof, and the receipt of signals thereto and transmission of signals therefrom.

In a preferred embodiment, the electronics module is also preferably programmed and configured to (i) receive and process the AC magnetic field strength signals that are generated and transmitted by the respiratory parameter monitoring sub-system, (ii) determine at least one respiratory parameter, more preferably, a plurality of respiratory parameters associated with the monitored subject as a function of the AC magnetic field strength signals, (iii) determine at least one respiratory parameter value as a function of the AC magnetic field strength signals, and (iv) determine at least one respiratory or sleep disorder as a function of the determined respiratory parameter and determined value thereof.

In some embodiments of the invention, the electronics module is also preferably programmed and configured to (i) receive and process the AC magnetic field strength signals that are generated and transmitted by the respiratory parameter monitoring sub-system and physiological parameter signals that are generated and transmitted by the physiological parameter monitoring sub-system, (ii) determine at least one respiratory parameter, more preferably, a plurality of respiratory parameters associated with the subject as a function of the AC magnetic field strength signals, (iii) determine at least one respiratory parameter value as a function of the AC magnetic field strength signals, and (iv) determine at least one respiratory or sleep disorder as a function of the physiological parameter value, and the determined respiratory parameter and determined value thereof.

In some embodiments of the invention, the electronics module is also preferably programmed and configured to (i) receive and process the AC magnetic field strength signals that are generated and transmitted by the respiratory parameter monitoring sub-system, the physiological parameter signals that are generated and transmitted by the physiological parameter monitoring sub-system, and accelerometer signals that are generated and transmitted by an accelerometer, (ii) determine at least one respiratory parameter, more preferably, a plurality of respiratory parameters associated with the subject as a function of the AC magnetic field strength signals, (iii) determine at least one respiratory parameter value as a function of the AC magnetic field strength signals, and (iv) determine at least one respiratory or sleep disorder as a function of the physiological parameter value, accelerometer data, and determined respiratory parameter and determined value thereof.

In some embodiments of the invention, the electronics module is also programmed to determine a physiological parameter value as a function of the physiological parameter signal.

In some embodiments of the invention, the electronics module is also programmed and configured to generate and transmit at least one sleep disorder warning signal as a function of (or in response to) a pre-determined respiratory parameter threshold value of the subject, i.e. a determined respiratory parameter and associated value of the subject, e.g. an apnea/hypopnea index (AHI) score in the range of 5-15 apneic events per hour, and/or physiological parameter threshold value, e.g. an $SpO_2$ level ≤95%.

In some embodiments of the invention, the respiratory and respiratory-physiological parameter monitoring systems further comprise a vibration device that is configured to receive the sleep disorder warning signal and generate vibrations at a pre-determined frequency in response to the sleep disorder warning signal.

In some embodiments of the invention, the respiratory and respiratory-physiological parameter monitoring systems further comprise an integral audio device that is configured to receive the sleep disorder warning signal and generate an audible signal at a pre-determined amplitude in response to the sleep disorder warning signal.

In some embodiments of the invention, the respiratory and respiratory-physiological parameter monitoring systems further comprise a remote audio device that is configured to receive the sleep disorder warning signal and generate an audible signal at a pre-determined amplitude in response to the sleep disorder warning signal.

In some embodiments of the invention, electronics module of the respiratory and respiratory-physiological parameter monitoring systems is also programmed and configured to transmit a verbal respiratory disorder warning to an emergency person or entity via a wireless link as a function of (or in response to) a pre-determined respiratory parameter threshold value and/or physiological parameter threshold value of the subject.

In some embodiments of the invention, the method for determining a sleep disorder of a subject with a respiratory parameter monitoring system generally comprises:

(i) providing a wearable respiratory parameter monitoring system comprising a respiratory parameter monitoring sub-system and an electronics control and processing module;

(ii) positioning the respiratory parameter monitoring system on the subject, wherein the respiratory parameter monitoring sub-system is positioned proximate the subject's xyphoid process and spine;

(iii) initiating the respiratory parameter monitoring system, wherein an AC magnetic field is generated by the permanent magnet of the respiratory parameter monitoring sub-system;

(iv) detecting and measuring variable magnetic field strengths in at least one field dimension of the AC magnetic field;

(v) generating AC magnetic field strength signals representing the measured AC magnetic field strengths;

(vi) transmitting the AC magnetic field strength signals to the electronics module;

(vii) determining at least one anatomical displacement of the subject as a function of the AC magnetic field strength signals with the electronics module;

(viii) determining at least one respiratory parameter as a function of the determined anatomical displacement with the electronics module;

(ix) determining a respiratory parameter value as a function of the AC magnetic field strength signals with the electronics module; and (x) determining a sleep disorder of the subject as a function of the determined respiratory parameter and value thereof with the electronics module.

In some embodiments of the invention, the first step in determining the sleep disorder with the respiratory parameter monitoring system is to pre-measure at least one respiratory parameter of the subject to determine a baseline respiratory parameter value.

In the noted embodiments, the sleep disorder of the subject is determined as a function of pre-measured baseline respiratory parameter value and the respiratory parameter and value thereof determined by the electronics module.

In some embodiments of the invention, the method for determining a sleep disorder of a subject with a respiratory-physiological parameter monitoring system generally comprises:

(i) providing a wearable respiratory-physiological parameter monitoring system comprising a respiratory parameter monitoring sub-system, physiological parameter monitoring sub-system and electronics control-processing module, the physiological parameter monitoring sub-system comprising at least one physiological parameter sensor;

(ii) positioning the respiratory-physiological parameter monitoring system on the subject, wherein the respiratory parameter monitoring sub-system is positioned proximate the subject's xyphoid process and spine;

(iii) initiating the respiratory-physiological parameter monitoring system, wherein an AC magnetic field is generated by the permanent magnet of the respiratory parameter monitoring sub-system;

(iv) detecting and measuring variable magnetic field strengths in at least one dimension of the AC magnetic field generated by the permanent magnet of the respiratory parameter monitoring sub-system;

(v) generating AC magnetic field strength signals representing the measured AC magnetic field strengths;

(vi) measuring at least one physiological parameter with the physiological parameter monitoring sub-system and generating a physiological parameter signal representing the physiological parameter and value thereof;

(vii) transmitting the AC magnetic field strength signals and physiological parameter signal to the electronics module;

(viii) determining at least one anatomical displacement of the subject as a function of the AC magnetic field strength signals with the electronics module;

(ix) determining at least one respiratory parameter of the subject as a function of the determined anatomical displacement with the electronics module;

(x) determining a respiratory parameter value as a function of the AC magnetic field strength signals with the electronics module; and (xi) determining a sleep disorder of the subject as a function of the physiological parameter value, and determined respiratory parameter and value thereof with the electronics module.

In some embodiments of the invention, the first step in determining the sleep disorder of the subject with the respiratory-physiological parameter monitoring system is to pre-measure at least one baseline respiratory parameter of the subject to determine a baseline.

In the noted embodiments, the sleep disorder of the subject is determined as a function of the pre-measured baseline respiratory parameter value, physiological parameter value, and the respiratory parameter and value thereof determined by the electronics module.

In some embodiments of the invention, the first step in determining the sleep disorder of the subject with the respiratory-physiological parameter monitoring system is to pre-measure at least one respiratory parameter of the subject to determine a baseline respiratory parameter value, and acquire baseline accelerometer data of the subject to establish the initial resting position parameters of the subject.

In the noted embodiments, the sleep disorder of the subject is determined as a function of the pre-measured baseline respiratory parameter value, physiological parameter value, the acquired baseline accelerometer data, and the respiratory parameter and value thereof determined by the electronics module.

In some embodiments of the invention, the sleep disorder comprises an apnea.

In some embodiments of the invention, the sleep disorder comprises hypopnea.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
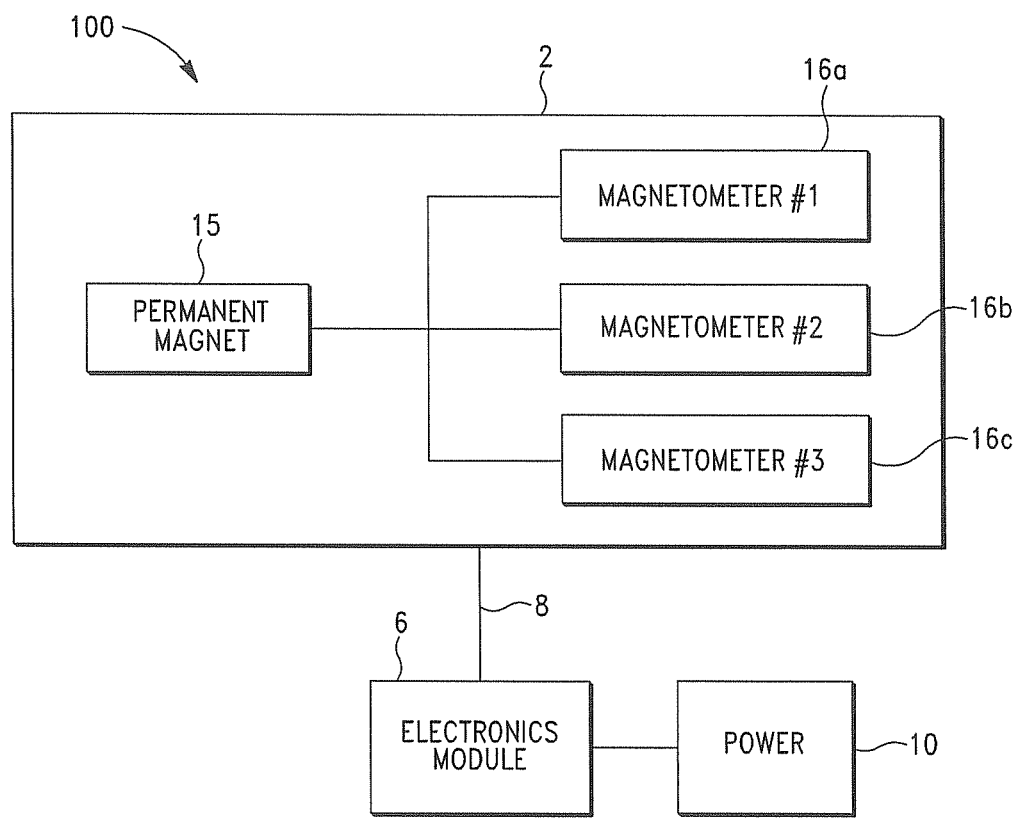
FIG. 1 is a schematic illustration of one embodiment of a respiratory parameter monitoring system, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an AC magnetic field strength signal" includes two or more such signals and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "respiratory parameter", "respiratory characteristic" and "respiration parameter" are used interchangeable herein, and mean and include a characteristic associated with the respiratory system and functioning thereof, including, without limitation, breathing frequency, tidal volume, inspiration volume, expiration volume, minute ventilation, inspiratory breathing time, expiratory breathing time, and flow rates (e.g., rates of change in the chest wall volume).

The terms "respiratory parameter", "respiratory characteristic" and "respiration parameter" further mean and include parameters associated with ventilation mechanics from correlated and counter-correlated movements of the chest wall compartments.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The term "apnea," as used herein, means and includes abnormal respiration, as defined herein, of a subject, which is characterized by at least one respiratory parameter and/or physiological characteristic.

The term "apnea" thus means and includes abnormal respiration characterized by, without limitation, breathing frequency or respiratory rate (f) (e.g., breaths per minute), tidal volume ($V_T$), inspiration volume, expiration volume, respiratory minute ventilation (e.g., inspiration volume per minute or expiration volume per minute) and/or peak expiratory flow rate.

The term "apnea" thus means and includes the inability of a subject to correctly modulate respiration.

The term "apnea" also means and includes, without limitation, an obstruction of the subject's upper airway.

The term "apnea" further means and includes abnormal respiration characterized by, without limitation, a seminal blood oxygen parameter and/or blood oxygen characteristic including, without limitation, oxyhemoglobin saturation and oxygen desaturation index of a subject, e.g. oxyhemoglobin desaturation events per hour.

The term "apnea" thus means and includes, without limitation, a reduction of a subject's oxyhemoglobin saturation level ≥5% of the subject's average normal oxyhemoglobin saturation level.

The term "apnea" also means and includes, without limitation, counter-correlated contraction and expansion of the subject's thoracic and abdominal regions during at least one respiration cycle, i.e. the expansion and contraction of the subject's thoracic and abdominal cavities are ~180° out of phase.

The term "apnea" also means and includes central sleep apnea and obstructive sleep apnea.

The term "apnea" also means and includes complex sleep apnea or mixed sleep apnea, i.e. a combination of central and obstructive sleep apnea.

The term "apneic event," as used herein, means and includes, without limitation, a reduction of a subject's minute ventilation ≥30% of the subject's average normal minute ventilation and/or a cessation in the subject's breathing ≥10 seconds with an attendant reduction in oxyhemoglobin saturation.

The term "normal respiration" as used herein in connection with "apnea" means and includes, without limitation, a "normal" or "healthy" apnea/hypopnea index (AHI), i.e. an AHI score ≤5 apneic events per hour of a subject's sleep, wherein an apneic event is defined as (i) a reduction of the subject's minute ventilation ≥30% of the subject's average normal minute ventilation and/or (ii) a cessation in the subject's breathing ≥10 seconds with an attendant reduction in oxyhemoglobin saturation.

The term "abnormal respiration," as used herein, means and includes, without limitation, cessation of a subject's breathing for a period ≥10 seconds with an attendant reduction in oxyhemoglobin saturation (or oxygen saturation).

The term "abnormal respiration" further means and includes, without limitation, a reduction of a subject's ventilation ≥30% of the subject's average normal ventilation.

The term "abnormal respiration" further means and includes, without limitation, a reduction of a subject's minute ventilation (V-dot) ≥30% of the subject's average normal minute ventilation.

The term "abnormal respiration" further means and includes, without limitation, a "mild" apnea/hypopnea index (AHI) score in the range of 5-15 apneic events per hour of a subject's sleep, wherein an apneic event is defined as (i) a reduction of the subject's minute ventilation ≥30% of the subject's average normal minute ventilation and/or (ii) a cessation in the subject's breathing ≥10 seconds with an attendant reduction in oxyhemoglobin saturation.

The term "abnormal respiration" further means and includes, without limitation, a "moderate" apnea/hypopnea index (AHI) score in the range of 15-30 events per hour of a subject's sleep, wherein an apneic event is defined as (i) a reduction of the subject's minute ventilation ≥30% of the subject's average normal minute ventilation and/or (ii) a cessation in the subject's breathing ≥10 seconds with an attendant reduction in oxyhemoglobin saturation.

The term "abnormal respiration" further means and includes, without limitation, a "severe" apnea/hypopnea index (AHI) score ≥30 events per hour of a subject's sleep, wherein an apneic event is defined as (i) a reduction of the subject's minute ventilation ≥30% of the subject's average normal minute ventilation and/or (ii) a cessation in the subject's breathing for a period of at least 10 seconds with an attendant reduction in oxyhemoglobin saturation.

The term "abnormal respiration" further means and includes, without limitation, a reduction of a subject's tidal volume ($V_T$) in the range of approximately 5-30% of the subject's average normal $V_T$.

The terms "sleep disorder" and "respiratory disorder" are used interchangeably herein, and mean and include, without limitation, an apnea, sleep apnea, hypopnea, and abnormal respiration.

The term "resting position" as used herein in connection with "apnea" and "sleep apnea" means and includes minimal physical activity or motion and/or the absence of physical activity or motion, except motion associated with normal breathing.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "subject" and "patient" also mean and include a wearer or user of a respiratory parameter monitoring system or a respiratory-physiological parameter monitoring system of the invention.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

Although the respiratory and respiratory-physiological parameter monitoring systems and associated methods for determining respiratory and physiological parameters, and respiratory disorders based thereon are described herein in connection with determining respiratory and physiological parameters, and respiratory and sleep disorders based thereon of a human subject, it is understood that the invention is not limited to such use. Indeed, the respiratory parameter monitoring system and respiratory-physiological parameter monitoring system and associated methods can also be readily employed to determine respiratory and physiological parameters, and respiratory and sleep disorders based thereon in other mammalian bodies.

The respiratory parameter and respiratory-physiological parameter monitoring systems and associated methods of the invention can also be employed in non-medical contexts, such as determining volumes and/or volume changes in extensible bladders used for containing liquids and/or gasses.

As indicated above, the present invention is directed to respiratory parameter and respiratory-physiological parameter monitoring systems and improved methods employing same for determining respiratory and sleep disorders based on measured strength variations in field dimensions of an AC magnetic field, and, hence, anatomical displacements based thereon, and, in some embodiments, physiological parameters and/or characteristics, and accelerometer data.

As discussed in detail below, in a preferred embodiment of the invention, the respiratory parameter monitoring system and respiratory-physiological parameter monitoring system comprise a wearable garment that is configured to cover at least the chest region and upper back of a wearer (or user).

As set forth in Co-Pending U.S. application Ser. No. 16/117,921, which is incorporated by reference herein in its entirety, in a preferred embodiment, the respiratory parameter monitoring system comprises a respiratory parameter monitoring sub-system, electronics module and integral signal transmission means associated therewith.

In a preferred embodiment, the respiratory-physiological parameter monitoring system similarly comprises a respiratory parameter monitoring sub-system, electronics module and integral signal transmission means associated therewith. However, as indicated above and discussed in detail below, the respiratory-physiological parameter monitoring system further comprises a physiological parameter monitoring sub-system.

In some embodiments, the respiratory parameter monitoring system and respiratory-physiological parameter monitoring system further comprise a spirometer.

As indicated above, in a preferred embodiment of the invention, the respiratory parameter monitoring sub-system comprises at least one permanent magnet configured to generate an AC magnetic field comprising a three-dimensional field and at least one magnetometer, which is configured and positioned to detect and measure the magnetic field strength in at least one of the AC magnetic field dimensions, and generate at least one AC magnetic field strength signal representing the measured magnetic field strength and, thereby, anatomical displacement of the monitored subject.

More preferably, the magnetometer is configured and positioned to detect and measure the magnetic field strengths in all three AC magnetic field dimensions, i.e. x, y and z dimensions, and generate a plurality of AC magnetic field strength signals representing the field strengths in all three AC magnetic field dimensions and, thereby, anatomical displacements of the monitored subject.

In some embodiments of the invention, the respiratory parameter monitoring sub-system comprises a plurality of paired permanent magnets and magnetometers, wherein the magnetometers are similarly configured and positioned to detect and measure the magnetic field strengths in at least one field dimension, more preferably, all three field dimensions of the AC magnetic fields generated by the permanent magnets, and generate a plurality of AC magnetic field strength signals representing the AC magnetic field strengths and, thereby, anatomical displacements of the monitored subject.

As discussed in detail below, in a preferred embodiment of the invention, the respiratory parameter monitoring sub-system comprises one (1) permanent magnet and three (3) paired magnetometers.

As also discussed in detail below, in a preferred embodiment, the permanent magnet is preferably positioned proximate a subject's xyphoid process, one magnetometer is positioned proximate a subject's umbilicus and the (2) additional magnetometers are positioned along a subject's spine in axial alignment with the subject's xyphoid process and umbilicus.

In a preferred embodiment, the anatomical displacements include three dimensional displacements of a subject's chest wall with respect to the subject's spine.

As indicated above, in a preferred embodiment of the invention, the physiological parameter monitoring sub-system comprises at least one physiological parameter sensor that is configured to (i) detect and measure a physiological parameter and, preferably, a value thereof, and (ii) generate a physiological parameter signal representing the measured physiological parameter and, preferably, value thereof.

In some embodiments, the physiological parameter monitoring sensor comprises a $SpO_2$ sensor.

In some embodiments, the physiological parameter monitoring sensor comprises a body temperature sensor.

In some embodiments of the invention, the physiological parameter monitoring sub-system further comprises at least one accelerometer that is configured and positioned to (i) establish the initial resting position parameters of a monitored subject, and (ii) monitor physical movement of the subject.

In some embodiments, the accelerometer comprises a conventional three (3) axis accelerometer that is configured to detect at least one accelerometer parameter in an X, Y and/or Z direction.

According to the invention, the accelerometer is configured to generate and transmit at least one accelerometer signal representing accelerometer data, including at least one accelerometer parameter.

In some embodiments, the accelerometer is preferably configured and positioned to generate a plurality of accelerometer signals that are processed and employed to determine whether a subject is in an erect, semi-erect, lateral lying, contralateral lying, supine or prone position.

As also indicated above, in a preferred embodiment, the electronics module is programmed and configured (i.e. comprises programs, parameters, instructions and at least one algorithm) to control the respiratory parameter and respiratory-physiological parameter monitoring systems and the function thereof, and the receipt of signals thereto and transmission of signals therefrom.

As further indicated above, in a preferred embodiment, the electronics module is also preferably programmed and configured to (i) receive and process the AC magnetic field strength signals that are generated and transmitted by the respiratory parameter sub-system, (ii) determine at least one respiratory parameter, more preferably, a plurality of respiratory parameters, associated with the subject as a function of the AC magnetic field strength signals, (iii) determine at least one respiratory parameter value as a function of the AC magnetic field strength signals, and (iv) determine at least one respiratory or sleep disorder as a function of the determined respiratory parameter and value thereof.

In some embodiments of the invention, the electronics module is further programmed and configured to (i) receive at least one respiratory parameter signal representing a pre-measured baseline respiratory parameter value, and (ii) determine at least one respiratory or sleep disorder as a function of the pre-measured baseline respiratory parameter value, and the respiratory parameter and value thereof determined as a function of the AC magnetic field strength signals.

In some embodiments of the invention, the electronics module is also preferably programmed and configured to (i) receive and process the AC magnetic field strength signals that are generated and transmitted by the respiratory parameter monitoring sub-system and physiological parameter signals that are generated and transmitted by the physiological parameter monitoring sub-system, (ii) determine at least one respiratory parameter, more preferably, a plurality of respiratory parameters associated with the subject as a function of the AC magnetic field strength signals, (iii) determine at least one respiratory parameter value as a function of the AC magnetic field strength signals, and (iv) determine at least one respiratory or sleep disorder as a function of the physiological parameter value, and the determined respiratory parameter and determined value thereof.

In some embodiments of the invention, the electronics module is also preferably programmed and configured to (i) receive and process the AC magnetic field strength signals that are generated and transmitted by the respiratory parameter monitoring sub-system, the physiological parameter signals that are generated and transmitted by the physiological parameter monitoring sub-system, and accelerometer signals that are generated and transmitted by an accelerometer, (ii) determine at least one respiratory parameter, more preferably, a plurality of respiratory parameters associated with the subject as a function of the AC magnetic field strength signals, (iii) determine at least one respiratory parameter value as a function of the AC magnetic field strength signals, and (iv) determine at least one respiratory or sleep disorder as a function of the physiological parameter value, accelerometer data, and determined respiratory parameter and determined value thereof.

In some embodiments of the invention, the electronics module is also programmed to determine a physiological parameter value as a function of the physiological parameter signal.

In some embodiments of the invention, the electronics module is also programmed and configured to generate and transmit at least one sleep disorder warning signal as a function of (or in response to) a pre-determined respiratory parameter threshold value and/or physiological parameter threshold value.

In some embodiments of the invention, the respiratory parameter monitoring system and/or respiratory-physiological parameter monitoring system further comprise a vibration device that is configured to receive the sleep disorder warning signal and generate vibrations at a pre-determined frequency or frequencies in response to the sleep disorder warning signal.

According to the invention, the vibration device can comprise various conventional vibration devices, including, without limitation, piezoelectric vibrators, eccentric cam motors and electromagnetic (EM) vibrators.

In a preferred embodiment of the invention, the vibration device is capable of generating vibrations with a frequency in the range of approximately 5-50 cycles per second (Hz).

In some embodiments, the vibration device is configured to generate a plurality of vibrations in a series of random or continuous pulses in intervals in the range of 1-30 seconds, more preferably, in intervals in the range of 1-3 seconds.

In some embodiments of the invention, the respiratory parameter monitoring system and/or respiratory-physiological parameter monitoring system further comprise a remote vibration device that is configured to receive the respiratory disorder warning signal and generate the vibrations referenced above in response to the sleep disorder warning signal.

According to the invention, the remote vibration device can comprise various conventional vibration devices, including, without limitation, piezoelectric vibrators, eccentric cam motors and electromagnetic (EM) vibrators.

In a preferred embodiment of the invention, the remote vibration device is capable of vibrating at a frequency in the range of approximately 5-50 Hz.

In some embodiments, the remote vibration device is similarly configured to generate a plurality of vibrations in a series of random or continuous pulses in intervals in the range of 1-30 seconds, more preferably, in intervals in the range of 1-3 seconds.

According to the invention, the respiratory parameter monitoring system and respiratory-physiological parameter monitoring system can comprise a plurality of vibration devices that are configured to generate and, hence, transmit the same or different vibrations.

In some embodiments, the respiratory parameter monitoring system and respiratory-physiological parameter monitoring system comprise a vibration device that is in communication with a subject's bed, such as a bed frame or mattress, or chair.

In some embodiments of the invention, the respiratory parameter monitoring system and/or respiratory-physiological parameter monitoring system further comprise an integral audio device that is configured to receive the respiratory disorder warning signal and produce an audible signal at a pre-determined amplitude in response to the sleep disorder warning signal.

According to the invention, the integral audio device can comprise various conventional audio devices, including, without limitation, piezoelectric audio devices and electromagnetic audio devices, e.g., speakers.

In a preferred embodiment of the invention, the audio device is capable of providing an audible signal with an amplitude in the range of approximately 70-90 dB.

In a preferred embodiment of the invention, the audio device is capable of generating acoustic signals with a frequency in the range of approximately 300-1200 Hz.

In some embodiments of the invention, the respiratory parameter monitoring system and/or respiratory-physiological parameter monitoring system further comprises a remote audio device that is configured to receive the sleep disorder warning signal and produce an audible signal at a pre-determined amplitude in response to the sleep disorder warning signal.

According to the invention, the remote audio device can similarly comprise various conventional audio devices, including, without limitation, piezoelectric audio devices and electromagnetic audio devices, e.g., speakers.

In a preferred embodiment of the invention, the remote audio device is capable of generating and transmitting an audible signal with an amplitude in the range of approximately 70-110 dB.

In a preferred embodiment of the invention, the remote audio device is capable of generating and transmitting acoustic signals with a frequency in the range of approximately 300-1200 Hz.

In some embodiments of the invention, electronics module of the respiratory parameter monitoring system and/or respiratory-physiological parameter monitoring system is also programmed and configured to transmit a sleep disorder warning comprising a pre-programmed verbal notice or warning in response to a pre-determined respiratory parameter threshold value and/or physiological parameter threshold value.

In some embodiments of the invention, the electronics module is programmed and configured to transmit the pre-programmed verbal warning to an emergency person or entity via a wireless link.

By way of example, in some embodiments, the electronics module is programmed to transmit the pre-programmed verbal warning to an emergency contact via a pre-programmed telephone number.

In some embodiments, the electronics module is programmed to transmit the pre-programmed verbal warning to an emergency service, e.g. police or fire department, via a pre-programmed emergency service telephone number, e.g., "911".

In a preferred embodiment of the invention, the electronics module is programmed and configured to provide a plurality of sleep disorder warning signals that induce multi-level excitation or warning events, i.e. vibrations of the vibration device at different frequencies, induced audible signals at different amplitudes and verbal warnings to emergency contacts and/or services, and combinations thereof, as a function of (or in response to) the pre-determined respiratory parameter threshold value and/or physiological parameter value.

Referring now to Table I, there is shown one embodiment of a single-level sleep disorder warning system of the invention. As illustrated in Table I, the single-level sleep disorder warning system preferably comprises at least one respiratory-physiological parameter threshold and at least one excitation event relating thereto.

TABLE I

| Alert Level | Respiratory-Physiological Parameter Threshold | Excitation Event |
|---|---|---|
| Level 1 | "Mild" apnea/hypopnea index (AHI) score in the range of 5-15 apneic events per hour of a subject's sleep. | A series of ~5-50 Hz vibrations comprising at least 1-3 pulses per second; preferably, sufficient to fully wake a subject. The vibrations transmitted until the subject wakes or turns off the vibration device. |

Referring now to Table II, there is shown one embodiment of a two-level sleep disorder warning system. As illustrated in Table II, the two-level sleep disorder warning system preferably comprises a plurality of respiratory-physiological parameter thresholds and at least one excitation event relating thereto.

TABLE II

| Alert Level | Respiratory-Physiological Parameter Threshold | Excitation Event |
|---|---|---|
| Level 1 | "Mild" apnea/hypopnea index (AHI) score in the range of 5-15 apneic events per hour of a subject's sleep. | A series of ~5-50 Hz vibrations comprising at least 1-3 pulses per second; preferably, sufficient to fully wake a subject. The vibrations transmitted until the subject wakes or turns off the vibration device. |
| Level 2 | "Moderate" apnea/hypopnea index (AHI) score in the range of 15-30 apneic events per hour of a subject's sleep. | A series of ~5-50 Hz vibrations comprising at least 1 pulse every two (2) seconds; preferably, sufficient to fully wake a subject and/or an audible signal of at least 70 dB produced by an integral audio device and/or remote device that steadily increases amplitude to a maximum of 90 dB until the subject wakes or turns off the vibration device and/or audible signal. |

Referring now to Table III, there is shown one embodiment of a three-level sleep disorder warning system. As illustrated in Table III, the three-level sleep disorder warning system similarly preferably comprises a plurality of respiratory-physiological parameter thresholds and at least one excitation event relating thereto.

TABLE III

| Alert Level | Respiratory-Physiological Parameter Threshold | Excitation Event |
|---|---|---|
| Level 1 | "Mild" apnea/hypopnea index (AHI) score in the range of 5-15 apneic events per hour of a subject's sleep. | A series of ~5-50 Hz vibrations comprising at least 1-3 pulses per second; preferably, sufficient to fully wake a subject. The vibrations transmitted until the subject wakes or turns off the vibration device. |
| Level 2 | "Moderate" apnea/hypopnea index (AHI) score in the range of 15-30 apneic events per hour of a subject's sleep. | A series of ~5-50 Hz vibrations comprising at least 1 pulse every two (2) seconds; preferably, sufficient to fully wake a subject and/or an audible signal of at least 70 dB produced by an integral audio device and/or remote device that steadily increases amplitude to a maximum of 90 dB until the subject wakes or turns off the |

TABLE III-continued

| Alert Level | Respiratory-Physiological Parameter Threshold | Excitation Event |
| --- | --- | --- |
| | | vibration device and/or audible signal. |
| Level 3 | "Severe" apnea/hypopnea index (AHI) score ≥30 apneic events per hour of a subject's sleep. | Transmittal of a verbal warning to an emergency contact and/or service, e.g., 911. |

Thus, in at least one embodiment of the invention the respiratory parameter monitoring system generally comprises a wearable garment that is configured to be removably positioned on a subject, the subject comprising thoracic and abdominal regions, a spine, an umbilicus and xyphoid process of the sternum, wherein when the wearable garment is positioned on a subject the wearable garment covers at least the thoracic and abdominal regions of the subject, the wearable garment comprising a respiratory parameter monitoring sub-system and an electronics module in communication therewith, the respiratory parameter monitoring sub-system comprising a permanent magnet and first, second and third magnetometers, the permanent magnet and the first, second and third magnetometers being positioned on the wearable garment, whereby, when the wearable garment is positioned on the subject, the permanent magnet is positioned proximate the subject's xyphoid process, the first magnetometer is positioned proximate the subject's umbilicus at a first magnetometer distance from the permanent magnet, the second magnetometer is positioned proximate a first anatomical region of the subject's spine opposite the subject's xyphoid process at a second magnetometer distance from the permanent magnet, the third magnetometer is positioned proximate a second anatomical region of the subject's spine opposite the subject's umbilicus at a third magnetometer distance from the permanent magnet, the permanent magnet being adapted to generate an alternating current (AC) magnetic field in first, second and third field dimensions, the first, second and third AC magnetic field dimensions comprising a first magnetic field frequency, the first AC magnetic field dimension comprising a first variable strength as a function of a first distance of the first magnetometer from the permanent magnet, a second variable strength as a function of a second distance of the second magnetometer from the permanent magnet and a third variable strength as a function of a third distance of the third magnetometer from the permanent magnet, the second AC magnetic field dimension comprising a fourth variable strength as a function of a fourth distance of the first magnetometer from the permanent magnet, a fifth variable strength as a function of a fifth distance of the second magnetometer from the permanent magnet and a sixth variable strength as a function of a sixth distance of the third magnetometer from the permanent magnet, the third AC magnetic field dimension comprising a seventh variable strength as a function of a seventh distance of the first magnetometer from the permanent magnet, a eighth variable strength as a function of an eighth distance of the second magnetometer from the permanent magnet and a ninth variable strength as a function of a ninth distance of the third magnetometer from the permanent magnet, the first magnetometer being configured to detect and measure the first, fourth and seventh variable strengths in the first, second and third AC magnetic field dimensions, the first magnetometer being further configured to generate a first AC magnetic field strength signal representing the first variable strength in the first AC magnetic field dimension, a second AC magnetic field strength signal representing the fourth variable strength in the second AC magnetic field dimension, and a third AC magnetic field strength signal representing the seventh variable strength in the third AC magnetic field dimension, and transmit the first, second and third AC magnetic field strength signals to the electronics module, the second magnetometer being configured to detect and measure the second, fifth and eighth variable strengths in the first, second and third AC magnetic field dimensions, the second magnetometer being further configured to generate a fourth AC magnetic field strength signal representing the second variable strength in the first AC magnetic field dimension, a fifth AC magnetic field strength signal representing the fifth variable strength in the second AC magnetic field dimension, and a sixth AC magnetic field strength signal representing the eighth variable strength in the third AC magnetic field dimension, and transmit the fourth, fifth and sixth AC magnetic field strength signals to the electronics module, the third magnetometer being configured to detect and measure the third, sixth and ninth variable strengths in the first, second and third AC magnetic field dimensions, the third magnetometer being further configured to generate a seventh AC magnetic field strength signal representing the third variable strength in the first AC magnetic field dimension, an eighth AC magnetic field strength signal representing the sixth variable strength in the second AC magnetic field dimension, and a ninth AC magnetic field strength signal representing the ninth variable strength in the third AC magnetic field dimension, and transmit the seventh, eighth and ninth AC magnetic field strength signals to the electronics module, the electronics module being adapted to receive the first, second and third AC magnetic field strength signals transmitted by the first magnetometer, the fourth, fifth and sixth AC magnetic field strength signals transmitted by the second magnetometer and the seventh, eighth and ninth AC magnetic field strength signals transmitted by the third magnetometer, the electronics module comprising a processing system that is programmed and configured to determine at least one respiratory parameter of the subject as a function of the first, second, third, fourth, fifth, sixth, seventh, eighth and ninth AC magnetic field strength signals, the processing system being further programmed and configured to determine a value of the at least one respiratory parameter of the subject as a function of the first, second, third, fourth, fifth, sixth, seventh, eighth and ninth AC magnetic field strength signals, the processing system being further programmed and configured to determine at least one respiratory or sleep disorder of the subject as a function of the at least one respiratory parameter value.

In some embodiments of the invention, wherein a baseline respiratory parameter value is pre-measured, the processing system is further programmed and configured to determine the respiratory or sleep disorder of the subject as a function of the pre-measured baseline respiratory parameter value and the determined respiratory parameter and value thereof.

In a preferred embodiment of the invention, the permanent magnet and the first magnetometer are in a first axial alignment, the permanent magnet and the second magnetometer are in a second axial alignment and the permanent magnet and the third magnetometer are in a third axial alignment.

In a preferred embodiment, the first, second, third, variable strengths of the first AC magnetic field represent displacement of the subject's first anatomical region with respect to the subject's xyphoid process.

In a preferred embodiment, the fourth, fifth and sixth variable strengths of the second AC magnetic field represent displacement of the subject's second anatomical region with respect to the subject's xyphoid process.

In a preferred embodiment, the seventh, eighth and ninth variable strengths of the third AC magnetic field represent displacement of the subject's third anatomical region with respect to the subject's xyphoid process.

In some embodiments of the invention, the permanent magnet and the first magnetometer are in axial alignment at a fourth magnetometer distance from the permanent magnet when the subject is in a first anatomical position and a fifth magnetometer distance from the permanent magnet when the subject is in a second anatomical position, the second position comprising an expanded thoracic region (or chest wall) of the subject.

In at least one embodiment of the invention the respiratory-physiological parameter monitoring system similarly comprises a wearable garment that is configured to be removably positioned on a subject, the subject comprising a spine, an umbilicus and xyphoid process of the sternum, wherein when the wearable garment is positioned on a subject the wearable garment covers at least a thoracic and abdominal region of the subject, the wearable garment comprising a respiratory parameter monitoring sub-system, physiological parameter sub-system and an electronics module, the respiratory parameter monitoring sub-system comprising a permanent magnet and first, second and third magnetometers, the physiological parameter sub-system comprising at least one physiological parameter sensor, the permanent magnet and the first, second and third magnetometers being positioned on the wearable garment, whereby, when the wearable garment is positioned on the subject, the permanent magnet is positioned proximate the subject's xyphoid process, the first magnetometer is positioned proximate the subject's umbilicus at a first magnetometer distance from the permanent magnet, the second magnetometer is positioned proximate a first anatomical region of the subject's spine opposite the subject's xyphoid process at a second magnetometer distance from the permanent magnet, the third magnetometer is positioned proximate a second anatomical region of the subject's spine opposite the subject's umbilicus at a third magnetometer distance from the permanent magnet, the permanent magnet being adapted to generate an alternating current (AC) magnetic field in first, second and third field dimensions, the first, second and third AC magnetic field dimensions comprising a first magnetic field frequency, the first AC magnetic field dimension comprising a first variable strength as a function of a first distance of the first magnetometer from the permanent magnet, a second variable strength as a function of a second distance of the second magnetometer from the permanent magnet and a third variable strength as a function of a third distance of the third magnetometer from the permanent magnet, the second AC magnetic field dimension comprising a fourth variable strength as a function of a fourth distance of the first magnetometer from the permanent magnet, a fifth variable strength as a function of a fifth distance of the second magnetometer from the permanent magnet and a sixth variable strength as a function of a sixth distance of the third magnetometer from the permanent magnet, the third AC magnetic field dimension comprising a seventh variable strength as a function of a seventh distance of the first magnetometer from the permanent magnet, a eighth variable strength as a function of an eighth distance of the second magnetometer from the permanent magnet and a ninth variable strength as a function of a ninth distance of the third magnetometer from the permanent magnet, the first magnetometer being configured to detect and measure the first, fourth and seventh variable strengths in the first, second and third AC magnetic field dimensions, the first magnetometer being further configured to generate a first AC magnetic field strength signal representing the first variable strength in the first AC magnetic field dimension, a second AC magnetic field strength signal representing the fourth variable strength in the second AC magnetic field dimension, and a third AC magnetic field strength signal representing the seventh variable strength in the third AC magnetic field dimension, and transmit the first, second and third AC magnetic field strength signals to the electronics module, the second magnetometer being configured to detect and measure the second, fifth and eighth variable strengths in the first, second and third AC magnetic field dimensions, the second magnetometer being further configured to generate a fourth AC magnetic field strength signal representing the second variable strength in the first AC magnetic field dimension, a fifth AC magnetic field strength signal representing the fifth variable strength in the second AC magnetic field dimension, and a sixth AC magnetic field strength signal representing the eighth variable strength in the third AC magnetic field dimension, and transmit the fourth, fifth and sixth AC magnetic field strength signals to the electronics module, the third magnetometer being configured to detect and measure the third, sixth and ninth variable strengths in the first, second and third AC magnetic field dimensions, the third magnetometer being further configured to generate a seventh AC magnetic field strength signal representing the third variable strength in the first AC magnetic field dimension, an eighth AC magnetic field strength signal representing the sixth variable strength in the second AC magnetic field dimension, and a ninth AC magnetic field strength signal representing the ninth variable strength in the third AC magnetic field dimension, and transmit the seventh, eighth and ninth AC magnetic field strength signals to the electronics module, the physiological parameter sensor being configured to detect and measure a physiological parameter, and transmit a physiological parameter signal representing the measured physiological parameter value to the electronics module, the electronics module being adapted to receive the first, second and third AC magnetic field strength signals transmitted by the first magnetometer, the fourth, fifth and sixth AC magnetic field strength signals transmitted by the second magnetometer and the seventh, eighth and ninth AC magnetic field strength signals transmitted by the third magnetometer, and the physiological parameter signal, the electronics module comprising a processing system that is programmed and configured to determine at least one respiratory parameter of the subject as a function of the first, second, third, fourth, fifth, sixth, seventh, eighth and ninth AC magnetic field strength signals, the processing system being further programmed and configured to determine a value of the at least one respiratory parameter of the subject as a function of the first, second, third, fourth, fifth, sixth, seventh, eighth and ninth AC magnetic field strength signals, the processing system being further programmed and configured to determine at least one respiratory or sleep disorder of the subject as a function of the physiological parameter value and the determined at least one respiratory parameter value.

In a preferred embodiment, the permanent magnet and the first magnetometer are similarly in a first axial alignment, the permanent magnet and the second magnetometer are in a second axial alignment and the permanent magnet and the third magnetometer are in a third axial alignment.

In some embodiments of the invention, wherein a baseline respiratory parameter value is pre-measured, the processing system is further programmed and configured to determine the respiratory or sleep disorder of the subject as a function of the pre-measured baseline respiratory parameter value, physiological parameter value, and the determined respiratory parameter and value thereof.

In some embodiments of the invention, wherein a baseline respiratory parameter value is pre-measured and baseline accelerometer data is acquired, the processing system is further programmed and configured to determine the respiratory or sleep disorder of the subject as a function of the pre-measured baseline respiratory parameter value, physiological parameter value, accelerometer data, and the determined respiratory parameter and value thereof.

As indicated above and discussed in detail below, in some embodiments of the invention, the method for determining a sleep disorder of a subject with a respiratory parameter monitoring system generally comprises:

(i) providing a wearable respiratory parameter monitoring system comprising a respiratory parameter monitoring sub-system and an electronics control and processing module;

(ii) positioning the respiratory parameter monitoring system on the subject, wherein the respiratory parameter monitoring sub-system is positioned proximate the subject's xyphoid process and spine;

(iii) initiating the respiratory parameter monitoring system, wherein an AC magnetic field is generated and transmitted by the permanent magnet of the respiratory parameter monitoring sub-system;

(iv) detecting and measuring variable magnetic field strengths in at least one field dimension of the AC magnetic field;

(v) generating AC magnetic field strength signals representing the measured AC magnetic field strengths;

(vi) transmitting the AC magnetic field strength signals to the electronics module;

(vii) determining at least one anatomical displacement of the subject as a function of the AC magnetic field strength signals with the electronics module;

(viii) determining at least one respiratory parameter as a function of the determined anatomical displacement with the electronics module;

(ix) determining a respiratory parameter value as a function of the AC magnetic field strength signals with the electronics module; and (x) determining a sleep disorder of the subject as a function of the determined respiratory parameter and value thereof with the electronics module.

In some embodiments of the invention, the first step in determining the sleep disorder of the subject with the respiratory parameter monitoring system is to pre-measure at least one respiratory parameter of the subject to determine a baseline respiratory parameter value.

In the noted embodiments, the sleep disorder of the subject is determined as a function of pre-measured baseline respiratory parameter value and the respiratory parameter and value thereof determined by the electronics module.

In some embodiments of the invention, the method for determining a sleep disorder of the subject with a respiratory-physiological parameter monitoring system generally comprises:

(i) providing a wearable respiratory-physiological parameter monitoring system comprising a respiratory parameter monitoring sub-system, physiological parameter monitoring sub-system and electronics control-processing module, the physiological parameter monitoring sub-system comprising at least one physiological parameter sensor;

(ii) positioning the respiratory-physiological parameter monitoring system on the subject, wherein the respiratory parameter monitoring sub-system is positioned proximate the subject's xyphoid process and spine;

(iii) initiating the respiratory-physiological parameter monitoring system, wherein an AC magnetic field is generated and transmitted by the permanent magnet;

(iv) detecting and measuring variable magnetic field strengths in at least one dimension of the AC magnetic field generated by the permanent magnet of the respiratory parameter monitoring sub-system;

(v) generating AC magnetic field strength signals representing the measured AC magnetic field strengths;

(vi) measuring at least one physiological parameter with the physiological parameter monitoring sub-system and generating a physiological parameter signal representing the physiological parameter and value thereof;

(vii) transmitting the AC magnetic field strength signals and physiological parameter signal to the electronics module;

(viii) determining at least one anatomical displacement of the subject as a function of the AC magnetic field strength signals with the electronics module;

(ix) determining at least one respiratory parameter of the subject as a function of the determined anatomical displacement with the electronics module;

(x) determining a respiratory parameter value as a function of the AC magnetic field strength signals with the electronics module; and (xi) determining a sleep disorder of the subject as a function of the physiological parameter value, and determined respiratory parameter and value thereof with the electronics module.

In some embodiments of the invention, the first step in determining the sleep disorder of the subject with the respiratory-physiological parameter monitoring system is similarly to pre-measure at least one baseline respiratory parameter of the user to determine a baseline respiratory parameter value of the subject.

In the noted embodiments, the sleep disorder of the subject is determined as a function of the pre-measured baseline respiratory parameter value, physiological parameter value, and the respiratory parameter and value thereof determined by the electronics module.

In some embodiments of the invention, the first step in determining the sleep disorder of the subject with the respiratory-physiological parameter monitoring system is to pre-measure at least one respiratory parameter of the user to determine a baseline respiratory parameter value, and acquire baseline accelerometer data of the subject to establish the initial resting position parameters of the subject.

In the noted embodiments, the sleep disorder of the subject is determined as a function of the pre-measured baseline respiratory parameter value, the acquired baseline accelerometer data, physiological parameter value, and the respiratory parameter and value thereof determined by the electronics module.

In a preferred embodiment of the invention, prior to acquiring the baseline accelerometer data, the accelerometer is calibrated according to the direction of gravitational force generated by Earth's gravity.

In some embodiments, the accelerometer data is processed and employed to determine whether a subject is in an erect, semi-erect, lateral lying, contralateral lying, supine or prone position.

In a preferred embodiment of the invention, the magnetometers are also calibrated according to accelerometer data representing the user is in at least one anatomical position, more preferably, a plurality of anatomical positions, e.g., erect, semi-erect, lateral lying, contralateral lying, supine and prone.

In a preferred embodiment, at least one baseline respiratory parameter is determined for the subject in at least one anatomical position, more preferably, a plurality of anatomical positions.

Referring now to FIG. 1, there is shown a schematic illustration of one embodiment of a respiratory parameter monitoring system of the invention. As illustrated in FIG. 1, the respiratory parameter monitoring system 100 preferably comprises a respiratory parameter monitoring sub-system 2, an electronics control and processing module 6, signal transmission conductors 8, and a power source 10, such as a battery.

As also illustrated in FIG. 1, the respiratory parameter monitoring sub-system 2 comprises a transmitter coil 15 and first, second and third magnetometers 16a, 16b, 16c.

In a preferred embodiment of the invention, the respiratory parameter monitoring system 100 preferably comprises a wearable garment that is configured to cover at least a portion of the torso of a subject, i.e. the thoracic and abdominal regions.

Figure 2:
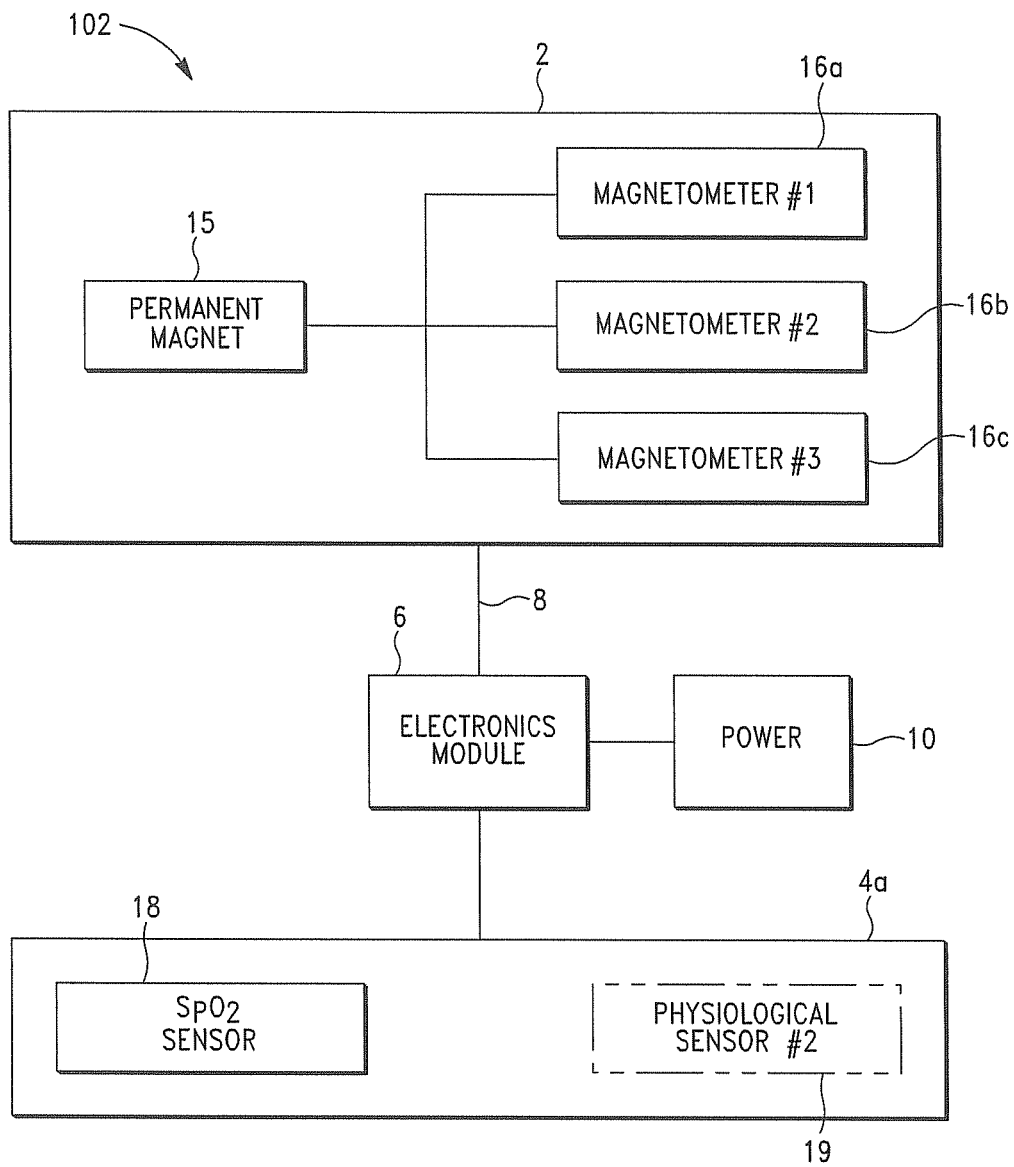
FIG. 2 is a schematic illustration of one embodiment of a respiratory-physiological parameter monitoring system, in accordance with the invention.

Referring now to FIG. 2, there is shown a schematic illustration of one embodiment of a respiratory-physiological parameter monitoring system of the invention. As illustrated in FIG. 2, the respiratory-physiological parameter monitoring system 102 similarly preferably comprises a respiratory parameter monitoring sub-system 2, electronics module 6, signal transmission conductors 8, and a power source 10.

As further illustrated in FIG. 2, the respiratory-physiological parameter monitoring system 102 further comprises a physiological parameter monitoring sub-system 4a of the invention.

In a preferred embodiment of the invention, the respiratory-physiological parameter monitoring system 102 similarly preferably comprises a wearable garment that is configured to cover at least a portion of the torso of a subject, i.e. the thoracic and abdominal regions.

Figure 5:
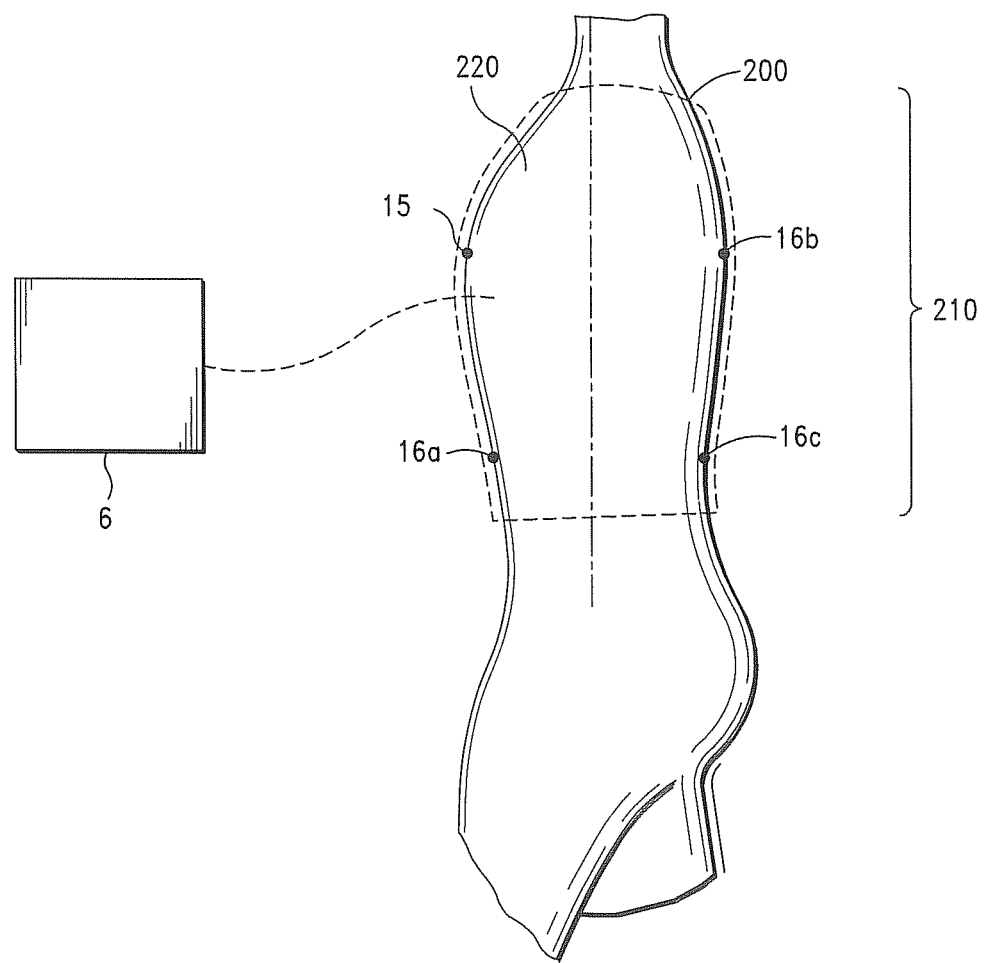
FIG. 5 is a side view of a subject, showing the position of a permanent magnet and three (3) magnetometers in a wearable respiratory-physiological parameter monitoring system and, thereby, on the subject, in accordance with one embodiment of the invention.

In a preferred embodiment of the invention, the respiratory parameter monitoring sub-system 2 of the respiratory-physiological parameter monitoring system 102 similarly comprises a transmitter coil 15 and first, second and third magnetometers 16a, 16b, 16c, which are preferably disposed at predetermined distances from the magnetometer 15 when disposed on a subject, as shown in FIG. 5.

In a preferred embodiment, the permanent magnet 16 comprises a rare earth magnet, including, but not limited to Neodymium ($Nd_2Fe_{14}B$) and Samarium-cobalt ($SmCo_5$).

As indicated above, the magnetometers 16a, 16b, 16c are configured and positioned to detect and measure strengths in the field dimensions of the AC magnetic field that is generated by the permanent magnet 16, and generate a plurality of AC magnetic field strength signals representing the field strengths in the AC magnetic field dimensions and, thereby, anatomical displacements of the monitored subject.

In embodiments of the invention, the respiratory parameter monitoring sub-system 2 comprises multiple paired magnetometers and permanent magnets, such as set forth in Applicant's Co-pending U.S. application Ser. No. 16/117,921.

In some embodiments, the respiratory parameter monitoring sub-system 2 comprises two (2) paired magnetometers and permanent magnets.

According to the invention, the permanent magnets, i.e. first and second permanent magnets, are configured and positioned on a subject (or user) such that the polarities of the permanent magnets are oriented perpendicular to each other, i.e. at a 90° angle relative to each other, wherein a net vector field, comprising at least X and Y vectors (or directions), of the magnetic fields is provided.

In a preferred embodiment of the invention, the magnetometers, i.e. first and second magnetometers, are configured to detect at least one magnetic field vector, more preferably, the first magnetometer is configured to detect at least one magnetic field vector in the X-direction and the second magnetometer is configured to detect at least one magnetic field vector in the Y-direction.

In embodiments of the invention, wherein the two-paired magnetometers and magnets are employed, when the magnetic field vectors in the X and Y directions are detected by the first and second magnetometers an angle between the X and Y magnetic field vectors and a net magnetic field vector based thereon is determined by the processing system of an electronics module. The angle between the X and Y magnetic field vectors and the net magnetic field vector are then used to determine at least one net magnetic field strength vector as a function of the dimensional distance between each magnetometer and its paired permanent magnet.

According to the invention, the net magnetic field strength vectors reflect a plurality of AC magnetic field strength signals representing a plurality of anatomical displacements of a monitored subject.

As indicated above, in a preferred embodiment of the invention, the physiological parameter monitoring sub-system 4a comprises at least one physiological parameter monitoring sensor.

As illustrated in FIG. 2, in some embodiments, the physiological parameter monitoring sensor 4a preferably comprises a $SpO_2$ sensor 18.

In some embodiments of the invention, the physiological parameter monitoring sub-system 4a comprises at least one additional physiological parameter monitoring sensor, such as a temperature sensor (shown in phantom and denoted 19).

As indicated above, in a preferred embodiment of the invention, the electronics module 6 preferably comprises a processing system or module, which is programmed and configured to control the respiratory-physiological parameter monitoring system 2 and the function thereof, and a data transmission module, which is programmed and configured to control the transmission and receipt of signals to and from the respiratory parameter monitoring sub-system 2 and physiological parameter monitoring sub-system 4a.

In a preferred embodiment of the invention, the processing system comprises at least one algorithm that is programmed and configured to isolate and process the AC magnetic field strength signals, and determine at least one respiratory parameter (or characteristic) of a subject as a function of the AC magnetic field strength signals.

In some embodiments of the invention, the processing system is further programmed and configured to pre-process the AC magnetic field strength signals to reduce or eliminate error associated with signal noise and/or interference from external sources and soft tissue motion.

In some embodiments, the pre-processing of the AC magnetic field strength signals is performed with a synchronous demodulator.

In some embodiments, the pre-processing of the AC magnetic field strength signals is performed with a band pass filter.

According to the invention, the processing system algorithm for determining a respiratory parameter (or characteristic) as a function of AC magnetic field strength signals can comprise various conventional algorithms, including, without limitation, a conventional and/or modified multiple-degree of freedom algorithm, including, without limitation, a two (2) degree of freedom algorithm and three (3) degree of freedom algorithm, a spectral density estimation algorithm using non-parametric methods, including, without limitation, singular spectrum analysis, short-time Fourier transform, cross-power method, transfer function estimate and magnitude squared coherence, and frequency domain algorithm, including, without limitation, a Fourier series algorithm, Fourier transform algorithm, Laplace transform algorithm, Z transform algorithm and wavelet transform algorithm.

In some embodiments, the processing algorithm comprises a machine learning algorithm, e.g., support vector machine (SVM) or neural network classifier, which is configured to differentiate between apneic events and non-apneic respiratory events, such as coughing.

In some embodiments, the machine learning algorithm that is further configured to differentiate between central, obstructive and complex sleep apnea based on a plurality of a subject's recorded epochs.

In some embodiments of the invention, the processing system is programmed and configured to generate and continuously update at least one diagnostic data set.

In a preferred embodiment, the diagnostic data set correlates at least one array of measured or determined respiratory parameters with at least one array of measured or determined anatomical displacement parameters of a subject.

Referring now to Table IV, there is shown an illustration of one embodiment of a diagnostic data set for a subject. As illustrated in Table IV, the diagnostic data set preferably comprises at least an array of measure or determined minute ventilation values and anatomical displacements measured at defined points on a subject during monitoring with a respiratory parameter or respiratory-physiological parameter monitoring system of the invention.

TABLE IV

| Subject #1 | | |
|---|---|---|
| Point No. | Minute Ventilation (V-dot) | Anatomical Displacement ($V_{M1}$, $V_{M2}$) |
| 0 | $V\text{-dot}_0$ | $(V_{M1}, V_{M2})_0$ |
| 1 | $V\text{-dot}_1$ | $(V_{M1}, V_{M2})_1$ |
| 2 | $V\text{-dot}_2$ | $(V_{M1}, V_{M2})_2$ |
| 3 | $V\text{-dot}_3$ | $(V_{M1}, V_{M2})_3$ |
| 4 | $V\text{-dot}_4$ | $(V_{M1}, V_{M2})_4$ |
| 5 | $V\text{-dot}_5$ | $(V_{M1}, V_{M2})_5$ |
| 6 | $V\text{-dot}_6$ | $(V_{M1}, V_{M2})_6$ |

According to the invention, the diagnostic data set shown in Table IV can be graphically presented, i.e. minute ventilation on the y-axis and anatomical displacement on the x-axis, and linearly interpolated using conventional equations, such as Eq. 1 shown below.

$$y = y_1 + (x - x_1)\frac{y_2 - y_1}{x_2 - x_1} \qquad \text{Eq. 1}$$

In a preferred embodiment, the processing system is programmed and configured to linearly interpolate a diagnostic data set, such as the diagnostic data set shown in Table IV, and determine the presence of at least one apneic event exhibited by a subject over a predetermined period of time and, thereby, a sleep disorder.

According to the invention, the diagnostic data set can be interpolated using any applicable methods and/or equations. In some embodiments, processing system is programmed and configured to interpolate a diagnostic data set using quadratic polynomial interpolation and determine the presence of at least one apneic event exhibited by a subject over a predetermined period of time and, thereby, a sleep disorder.

In some embodiments of the invention, a subject's tidal volume ($V_T$) and respiratory rate (f) are determined via spirometry. Minute ventilation (V-dot) can then be determined using the equation shown below.

$$V\text{-dot} = V_T \times f \qquad \text{Eq. 2}$$

In a preferred embodiment of the invention, the processing system is further programmed to differentiate between indicia of a sleep disorder, i.e. respiratory and/or physiological parameters indicative of a sleep disorder, and extraneous respiratory events, such as coughing, hiccups, sneezing, etc. by, for example, comparing the pre-measured baseline respiratory and pre-measured baseline physiological parameters of the subject in a resting position to pre-determined respiratory and physiological parameter threshold values reflecting a respiratory disorder.

In a preferred embodiment of the invention, the processing system is further programmed to determine a type of sleep apnea, i.e. obstructive sleep apnea, central sleep apnea and complex sleep apnea, based on detected anatomical displacements of a monitored subject (or user).

In some embodiments, the processing system determines the type of sleep apnea of a subject based on the correlation or synchrony between the expansion and contraction of the subject's thoracic and abdominal regions (or chest wall and abdominal wall) during at least one respiratory cycle.

As is well established, when a subject is afflicted with obstructive sleep apnea, the subject will exhibit a counter-correlated expansion and contraction of the thoracic and abdominal regions, i.e. the expansion and contraction of the thoracic and abdominal regions are ~180° out of phase, during at least one respiratory cycle.

As is also well established, when a subject is afflicted with central sleep apnea, the subject will exhibit a complete absence of thoracic and abdominal region expansion and contraction.

Thus, according to the invention, when the AC magnetic field strength signals reflect counter-correlated expansion and contraction of a subject's thoracic and abdominal regions during at least one respiratory cycle, a determination of obstructive sleep apnea is provided.

When the AC magnetic field strength signals reflect the absence of thoracic and abdominal region expansion and contraction, a determination of central sleep apnea is provided.

In a preferred embodiment of the invention, the electronics module 6 further comprises a data transmission sub-system that is programmed and configured to control the transmission of signals from the respiratory parameter monitoring sub-system 2 and physiological parameter monitoring sub-system 4a.

In some embodiments, the data transmission sub-system is also preferably programmed and configured to transmit the respiratory parameter signals to a remote signal receiving device, e.g., a base module or a hand-held electronic device, such as a smart phone, tablet or computer. In some embodiments, the remote signal receiving device is programmed and configured to display received and/or processed signals, e.g., respiration parameter signals, physiological parameter signals and accelerometer data received from the electronics module 6.

As further illustrated in FIG. 2, the respiratory-physiological parameter monitoring system 102 also similarly includes signal transmission conductors 8, which facilitate connection and, thereby, signal communication by and between the respiratory parameter monitoring sub-system 2, physiological parameter monitoring sub-system 4a, and electronics module 6.

Figure 3:
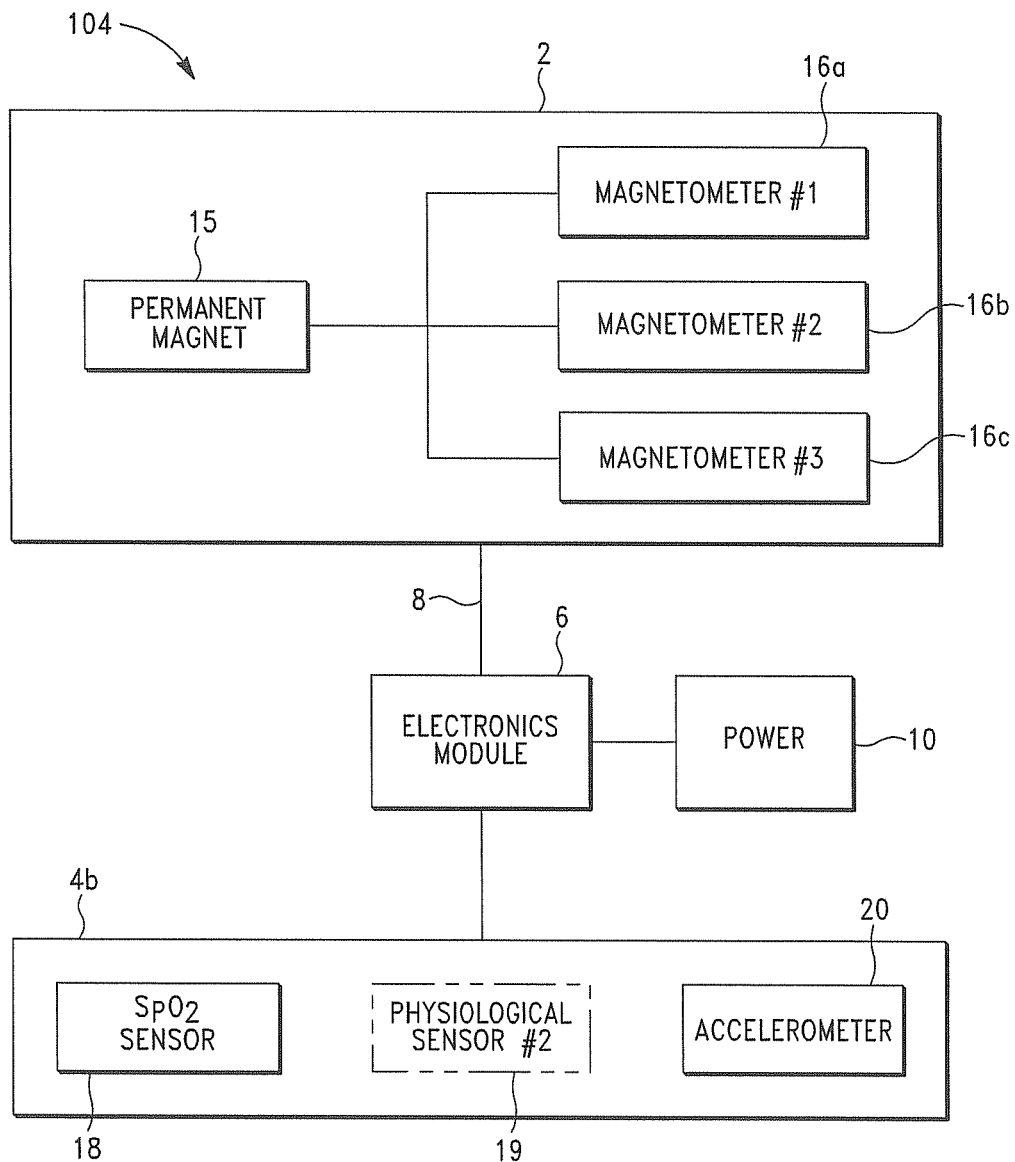
FIG. 3 is a schematic illustration of another embodiment of a respiratory-physiological parameter monitoring system, in accordance with the invention.

Referring now to FIG. 3, there is shown a schematic illustration of another embodiment of a respiratory-physiological parameter monitoring system of the invention. As illustrated in FIG. 3, the respiratory-physiological parameter monitoring system 104 similarly preferably comprises a respiratory parameter monitoring sub-system 2, a physiological parameter monitoring sub-system comprising at least one physiological parameter sensor, electronics control and processing module 6, signal transmission conductors 8, and a power source 10, such as embodied in the respiratory-physiological parameter monitoring system 102 described above.

As further illustrated in FIG. 3, in this embodiment, the physiological parameter monitoring sub-system (now denoted "4b") further comprises an accelerometer 20 that is configured and positioned to monitor physical movement of the subject.

In this embodiment, the processing system of the electronics module 6 is also programmed to determine a sleep disorder as a function of measured respiratory and physiological parameters, and accelerometer data of the subject.

Figure 4:
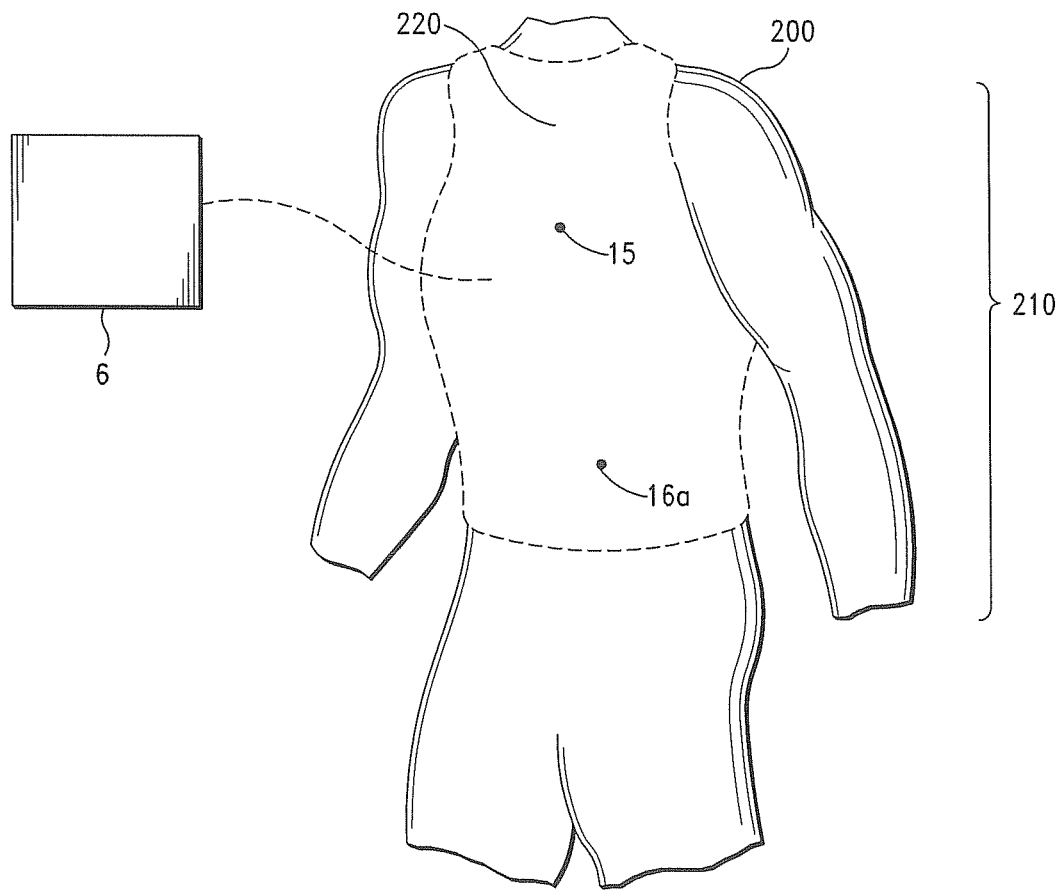
FIG. 4 is a perspective view of one embodiment of a wearable respiratory-physiological parameter monitoring system positioned on a subject showing the position of a permanent magnet proximate the xyphoid process and one (1) magnetometer proximate the umbilicus, in accordance with the invention.

Referring now to FIG. 4, there is shown an embodiment of a wearable garment 220 that can incorporate a respiratory parameter monitoring system 100 or respiratory-physiological parameter monitoring system 102 of the invention.

As indicated above and illustrated in FIG. 4, the wearable garment 220 is preferably configured to cover at least the upper torso 210, i.e. the thoracic and abdominal regions, of a subject 200.

According to the invention, the wearable garment 220 can, however, also be configured to cover other regions of the subject 200, including, without limitation, the lower abdominal region.

As illustrated in FIG. 5, in a preferred embodiment, when the wearable garment 220 incorporates a respiratory parameter monitoring system 100 or respiratory-physiological parameter monitoring system 102 of the invention (and, hence, forms a wearable monitoring system) and is positioned on the upper torso 210 of a subject, the permanent magnet 15 is preferably positioned proximate the subject's xyphoid process and the first magnetometer 16a is positioned proximate the umbilicus, the second magnetometer 16b is positioned proximate the subject's spine opposite the permanent magnet 15, and the third magnetometer 16c is positioned proximate the subject's spine opposite the umbilicus.

As discussed in detail below, when the noted wearable monitoring system is positioned proximate the upper torso 210 of a subject 200 and the monitoring system is initiated, sleep disorders of the subject 200 can be accurately determined.

The methods for determining a sleep disorder with the respiratory and respiratory-physiological parameter monitoring systems will now be described in detail.

As indicated above, in some embodiments of the invention, the first step in determining a sleep disorder with a respiratory parameter monitoring system or respiratory-physiological monitoring system of the invention is to (i) pre-measure at least one baseline parameter of the subject.

After the baseline respiratory parameter of the subject is measured, the next step is to (ii) select or provide the desired respiratory parameter or respiratory-physiological parameter monitoring system.

In this instance, a wearable respiratory parameter monitoring system comprising a wearable system comprising respiratory parameter monitoring system 100 shown in FIG. 1 is selected.

After the wearable respiratory parameter monitoring system is selected and, hence, provided, (iii) the respiratory parameter monitoring system is positioned on the upper torso of a subject, wherein the permanent magnet 15 is positioned proximate the subject's xyphoid process, the first magnetometer 16a is positioned proximate the subject's umbilicus at a first magnetometer distance from the permanent magnet 15, the second magnetometer 16b is positioned proximate a first anatomical region of the subject's spine opposite the subject's xyphoid process at a second magnetometer distance from the permanent magnet 15, the third magnetometer 16c is positioned proximate a second anatomical region of the subject's spine opposite the subject's umbilicus at a third magnetometer distance from the permanent magnet 15.

After the respiratory parameter monitoring system 100 is positioned on a subject, (iv) the wearable respiratory parameter monitoring system is initiated, i.e. powered-up.

As indicated above, when the respiratory parameter monitoring system is initiated, i.e. powered-up, the permanent magnet generates and transmits an AC magnetic field.

After the system is initiated and the permanent magnet transmits the AC magnetic field, (v) field strengths in at least one dimension (more preferably, all three field dimensions) of the AC magnetic field are detected and measured by the respiratory parameter monitoring sub-system 2, i.e. magnetometers 16a, 16b, 16c.

After the field strengths in the AC magnetic field dimensions are measured, (vi) AC magnetic field strength signals representing the AC magnetic field strengths are generated and transmitted to the electronics module 6.

After the AC magnetic field strength signals are transmitted to the electronics module 6, (vii) at least one anatomical displacement of the subject is determined as a function of the AC magnetic field strength signals by the electronics module 6.

As indicated above, the electronics module comprises at least one algorithm that is programmed and configured to isolate and process the AC magnetic field strength signals, and determine at least one anatomical displacement of the wearer, i.e. subject, as a function of the AC magnetic field strength signals.

After the anatomical displacement of the subject is determined, (viii) a physiological parameter of the subject is determined as a function of the determined anatomical displacement by the electronics module 6.

After the physiological parameter of the subject is determined, (ix) a respiratory parameter value is determined as a function of the AC magnetic field strength signals by the electronics module 6.

After the respiratory parameter value is determined, (x) a sleep disorder is determined as a function of the pre-measured baseline respiratory parameter value and determined respiratory parameter and value thereof.

If the desired monitoring system comprises a wearable respiratory-physiological parameter monitoring system comprising monitoring system 102 shown in FIG. 2, the method for determining a respiratory disorder similarly preferably comprises (i) pre-measuring at least one baseline respiratory parameter of the subject or user, (ii) positioning the wearable respiratory-physiological parameter monitoring system on the upper torso of the subject, and (iii) initiating the wearable respiratory-physiological parameter monitoring system.

As indicated above, when the wearable respiratory parameter monitoring system is initiated, the permanent magnet generates and transmits an AC magnetic field.

After the system is initiated and the permanent magnet transmits the AC magnetic field, (iv) field strengths in at least one field dimension (more preferably, all three field dimensions) of the AC magnetic field are similarly detected and measured by the respiratory parameter monitoring sub-system 2, i.e. magnetometers 16a, 16b, 16c.

After the field strengths in the AC magnetic field dimensions are measured, (v) AC magnetic field strength signals representing the AC magnetic field strengths are generated by the respiratory parameter monitoring sub-system 2.

Simultaneous or after the field strengths in the AC magnetic field dimensions are measured, (vi) a physiological parameter is also measured by the physiological parameter monitoring sub-system 4a, i.e. physiological parameter sensor.

After the physiological parameter is measured by the physiological parameter monitoring sub-system 4a, (vii) a physiological parameter signal representing the measured physiological parameter is generated by physiological parameter monitoring sub-system 4a, i.e. physiological parameter sensor.

After the AC magnetic field strength signals and physiological parameter signal are generated, (viii) the AC magnetic field strength signals and the physiological parameter signal are transmitted to the electronics module 6.

After the AC magnetic field strength signals and physiological parameter signal are transmitted to the electronics module 6, (ix) at least one anatomical displacement of the subject is determined as a function of the AC magnetic field strength signals by the electronics module 6.

After the anatomical displacement is determined, (x) at least one respiratory parameter of the subject is determined as a function of the anatomical displacement by the electronics module 6.

After the respiratory parameter is determined, (xi) at least one respiratory parameter value is determined as a function of the AC magnetic field strength signals by the electronics module 6.

After the respiratory parameter value is determined, (x) a sleep disorder is determined as a function of the pre-measured baseline respiratory parameter value, physiological parameter value, and determined respiratory parameter and value thereof.

If the desired monitoring system comprises a wearable respiratory-physiological parameter monitoring system comprising monitoring system 104 shown in FIG. 3, the first step in determining a respiratory disorder includes also acquiring base-line accelerometer data to establish the initial resting position and movement of the subject.

As indicated above, in some embodiments, the baseline accelerometer data is then employed with pre-measured baseline physiological parameter value, physiological parameter value, and determined respiratory parameter and value thereof to determine the sleep disorder.

As indicated above, in some embodiments of the invention, the sleep disorder comprises an apnea.

In some embodiments of the invention, the sleep disorder comprises hypopnea.

As will readily be appreciated by one having ordinary skill in the art, the present invention provides numerous advantages compared to prior art methods and systems for detecting anatomical displacements and determining respiratory characteristics and respiratory disorders therefrom. Among the advantages are (i) the provision of respiration and respiration-physiological monitoring systems that accurately monitor and measure anatomical displacements and physiological characteristics of a subject, and (ii) methods for accurately determining multiple respiratory disorders and sleeping disorders based on anatomical displacement and physiological characteristic data that is detected and measured by the respiration and respiration-physiological monitoring systems.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A wearable monitoring system, comprising:
a wearable garment that is configured to be removably positioned on a subject, said subject comprising thoracic and abdominal regions, a spine, an umbilicus and xyphoid process of the sternum, wherein when said wearable garment is positioned on a subject said wearable garment covers at least said thoracic and abdominal regions of said subject,
said wearable garment comprising a respiratory parameter monitoring sub-system and an electronics module in communication therewith,
said respiratory parameter monitoring sub-system comprising a permanent magnet and first, second and third magnetometers,
said permanent magnet and said first, second and third magnetometers being positioned on said wearable garment, whereby, when said wearable garment is positioned on said subject, said permanent magnet is positioned proximate said subject's xyphoid process, said first magnetometer is positioned at a first anatomical region of said subject proximate said subject's umbilicus at a first magnetometer distance from said permanent magnet, said second magnetometer is positioned at a second anatomical region of said subject proximate said subject's spine opposite said subject's xyphoid process at a second magnetometer distance from said permanent magnet, said third magnetometer is positioned at a third anatomical region of said subject proximate said subject's spine opposite said subject's umbilicus at a third magnetometer distance from said permanent magnet, said permanent magnet being adapted to generate an alternating current (AC) magnetic field in first, second and third field dimensions, said first, second and third AC magnetic field dimensions comprising a first magnetic field frequency, said first AC magnetic field dimension comprising a first variable field strength as a function of a first distance of said first magnetometer from said permanent magnet, a second variable field strength as a function of a second distance of said second magnetometer from said permanent magnet and a third variable field strength as a function of a third distance of said third magnetometer from said permanent magnet, said second AC magnetic field dimension comprising a fourth variable field strength as a function of a fourth distance of said first magnetometer from said permanent magnet, a fifth variable field strength as a function of a fifth distance of said second magnetometer from said permanent magnet and a sixth variable strength as a function of a sixth distance of said third magnetometer from said permanent magnet, said third AC magnetic field dimension comprising a seventh variable field strength as a function of a seventh distance of said first magnetometer from said permanent magnet, a eighth variable field strength as a function of an eighth distance of said second magnetometer from said permanent magnet and a ninth variable field strength as a function of a ninth distance of said third magnetometer from said permanent magnet, said first magnetometer being configured to detect and measure said first, fourth and seventh variable field strengths in said first, second and third AC magnetic field dimensions, said first magnetometer being further configured to generate a first AC magnetic field strength signal representing said first variable field strength in said first AC magnetic field dimension, a second AC magnetic field strength signal representing said fourth variable field strength in said second AC magnetic field dimension, and a third AC magnetic field strength signal representing said seventh variable field strength in said third AC magnetic field dimension, and transmit said first, second and third AC magnetic field strength signals to said electronics module, said second magnetometer being configured to detect and measure said second, fifth and eighth variable field strengths in said first, second and third AC magnetic field dimensions, said second magnetometer being further configured to generate a fourth AC magnetic field strength signal representing said second variable field strength in said first AC magnetic field dimension, a fifth AC magnetic field strength signal representing said fifth variable field strength in said second AC magnetic field dimension, and a sixth AC magnetic field strength signal representing said eighth variable field strength in said third AC magnetic field dimension, and transmit said fourth, fifth and sixth AC magnetic field strength signals to said electronics module, said third magnetometer being configured to detect and measure said third, sixth and ninth variable field strengths in said first, second and third AC magnetic field dimensions, said third magnetometer being further configured to generate a seventh AC magnetic field strength signal representing said third variable field strength in said first AC magnetic field dimension, an eighth AC magnetic field strength signal representing said sixth variable field strength in said second AC magnetic field dimension, and a ninth AC magnetic field strength signal representing said ninth variable field strength in said third AC magnetic field dimension, and transmit said seventh, eighth and ninth AC magnetic field strength signals to said electronics module, said electronics module being adapted to receive said first, second and third AC magnetic field strength signals transmitted by said first magnetometer, said fourth, fifth and sixth AC magnetic field strength signals transmitted by said second magnetometer and said seventh, eighth and ninth AC magnetic field strength signals transmitted by said third magnetometer, said electronics module comprising a processing system that is programmed and configured to determine at least one respiratory parameter of said subject as a function of said first, second, third, fourth, fifth, sixth, seventh, eighth and ninth AC magnetic field strength signals, said processing system being further programmed and configured to determine a value of said at least one respiratory parameter of said subject as a function of said first, second, third, fourth, fifth, sixth, seventh, eighth and ninth AC magnetic field strength signals, said processing system being further programmed and configured to determine a sleep disorder of said subject as a function of said determined at least one respiratory parameter and said determined value thereof.

2. The monitoring system of claim 1, wherein said permanent magnet and said first magnetometer are in a first axial alignment, said permanent magnet and said second magnetometer are in a second axial alignment and said permanent magnet and said third magnetometer are in a third axial alignment.

3. The monitoring system of claim 2, wherein said first, second and third variable strengths of said first AC magnetic field represent displacement of said subject's first anatomical region with respect to said subject's xyphoid process.

4. The monitoring system of claim 2, wherein said fourth, fifth and sixth variable strengths of said second AC magnetic field represent displacement of said subject's second anatomical region with respect to said subject's xyphoid process.

5. The monitoring system of claim 2, wherein said seventh, eighth and ninth variable strengths of said third AC magnetic field represent displacement of said subject's third anatomical region with respect to said subject's xyphoid process.

6. The monitoring system of claim 1, wherein said wearable garment further comprises a physiological parameter monitoring sub-system.

7. The monitoring system of claim 6, wherein said physiological parameter monitoring sub-system comprises at least one physiological parameter sensor that is adapted to measure a physiological parameter of said subject and transmit a physiological parameter signal representing said physiological parameter and a value of same.

8. The monitoring system of claim 7, wherein said electronics module is further adapted to receive said physiological parameter signal transmitted by said physiological parameter sensor, and wherein said electronics module is further programmed to determine said sleep disorder of said subject as a function of said determined at least one respiratory parameter and said determined value thereof, and said physiological parameter value.

9. The monitoring system of claim 6, wherein said physiological parameter monitoring sub-system comprises at least one accelerometer that is configured to measure accelerometer data representing anatomical displacement of said subject and generate and transmit an accelerometer parameter signal representing said measured accelerometer data.

10. The monitoring system of claim 9, wherein said electronics module is further adapted to receive said physiological parameter signal transmitted by said physiological parameter monitoring sensor and said accelerometer parameter signal transmitted by said accelerometer, and wherein said electronics module is further programmed to determine said sleep disorder of said subject as a function of said determined at least one respiratory parameter and said determined value thereof, said physiological parameter value and said accelerometer data.

11. The monitoring system of claim 1, wherein said sleep disorder comprises an apnea.

12. The monitoring system of claim 1, wherein said processing system is further programmed and configured to generate at least one sleep disorder warning signal that induces an excitation event when said determined at least one respiratory parameter exceeds a predetermined respiratory parameter threshold.

13. The monitoring system of claim 12, wherein said at least one respiratory parameter comprises said subject's apnea/hypopnea index (AHI) and said predetermined respiratory parameter threshold comprises an AHI score in the range of 5-15 apneic events per hour of said subject's sleep.

14. The monitoring system of claim 12, wherein said at least one respiratory parameter comprises said subject's minute ventilation and said predetermined respiratory parameter threshold comprises a reduction of said subject's minute ventilation of at least 30% of said subject's average normal minute ventilation.

15. The monitoring system of claim 12, wherein said at least one respiratory parameter comprises said subject's breathing rate and said predetermined respiratory parameter threshold comprises cessation in said subject's breathing for at least 10 seconds.

16. The monitoring system of claim 12, wherein said wearable garment further comprises a vibration device, and wherein said excitation event comprises generation of vibrations by said vibration device in the range of 5-50 Hz.

17. The monitoring system of claim 16, wherein said vibrations comprise a series of random pulses of at least 1-3 pulses per second.

18. The monitoring system of claim 16, wherein said vibrations comprise a series of uniform pulses of at least 1-3 pulses per second.

19. A method for determining a sleep disorder, comprising the steps of:
(i) providing a wearable monitoring system comprising a wearable garment that is configured to be removably positioned on a subject, said subject comprising thoracic and abdominal regions, a spine, an umbilicus and xyphoid process of the sternum, wherein when said wearable garment is positioned on a subject said wearable garment covers at least said thoracic and abdominal regions of said subject, said wearable monitoring system comprising a respiratory parameter monitoring sub-system and an electronics module in communication therewith, said respiratory parameter monitoring sub-system comprising a permanent magnet and first, second and third magnetometers, said permanent magnet and said first, second and third magnetometers being positioned on said wearable garment, whereby, when said wearable garment is positioned on said subject, said permanent magnet is positioned proximate said subject's xyphoid process, said first magnetometer is positioned at a first anatomical region of said subject proximate said subject's umbilicus at a first magnetometer distance from said permanent magnet, said second magnetometer is positioned at a second anatomical region of said subject proximate said subject's spine opposite said subject's xyphoid process at a second magnetometer distance from said permanent magnet, said third magnetometer is positioned at a third anatomical region of said subject proximate said subject's spine opposite said subject's umbilicus at a third magnetometer distance from said permanent magnet, said permanent magnet being adapted to generate an alternating current (AC) magnetic field in first, second and third field dimensions, said first, second and third AC magnetic field dimensions comprising a first magnetic field frequency, said first AC magnetic field dimension comprising a first variable field strength as a function of a first distance of said first magnetometer from said permanent magnet, a second variable field strength as a function of a second distance of said second magnetometer from said permanent magnet and a third variable field strength as a function of a third distance of said third magnetometer from said permanent magnet, said second AC magnetic field dimension comprising a fourth variable field strength as a function of a fourth distance of said first magnetometer from said permanent magnet, a fifth variable field strength as a function of a fifth distance of said second magnetometer from said permanent magnet and a sixth variable strength as a function of a sixth distance of said third magnetometer from said permanent magnet, said third AC magnetic field dimension comprising a seventh variable field strength as a function of a seventh distance of said first magnetometer from said permanent magnet, a eighth variable field strength as a function of an eighth distance of said second magnetometer from said permanent magnet and a ninth variable field strength as a function of a ninth distance of said third magnetometer from said permanent magnet, said first magnetometer being configured to detect and measure said first, fourth and seventh variable field strengths in said first, second and third AC magnetic field dimensions, said first magnetometer being further configured to generate a first AC magnetic field strength signal representing said first variable field strength in said first AC magnetic field dimension, a second AC magnetic field strength signal representing said fourth variable field strength in said second AC magnetic field dimension, and a third AC magnetic field strength signal representing said seventh variable field strength in said third AC magnetic field dimension, and transmit said first, second and third AC magnetic field strength signals to said electronics module, said second magnetometer being configured to detect and measure said second, fifth and eighth variable field strengths in said first, second and third AC magnetic field dimensions, said second magnetometer being further configured to generate a fourth AC magnetic field strength signal representing said second variable field strength in said first AC magnetic field dimension, a fifth AC magnetic field strength signal representing said fifth variable field strength in said second AC magnetic field dimension, and a sixth AC magnetic field strength signal representing said eighth variable field strength in said third AC magnetic field dimension, and transmit said fourth, fifth and sixth AC magnetic field strength signals to said electronics module, said third magnetometer being configured to detect and measure said third, sixth and ninth variable field strengths in said first, second and third AC magnetic field dimensions, said third magnetometer being further configured to generate a seventh AC magnetic field strength signal representing said third variable field strength in said first AC magnetic field dimension, an eighth AC magnetic field strength signal representing said sixth variable field strength in said second AC magnetic field dimension, and a ninth AC magnetic field strength signal representing said ninth variable field strength in said third AC magnetic field dimension, and transmit said seventh, eighth and ninth AC magnetic field strength signals to said electronics module, said electronics module being adapted to receive said first, second and third AC magnetic field strength signals transmitted by said first magnetometer, said fourth, fifth and sixth AC magnetic field strength signals transmitted by said second magnetometer and said seventh, eighth and ninth AC magnetic field strength signals transmitted by said third magnetometer, said electronics module comprising a processing system that is programmed and configured to determine at least one respiratory parameter of said subject as a function of said first, second, third, fourth, fifth, sixth, seventh, eighth and ninth AC magnetic field strength signals, said processing system being further programmed and configured to determine a value of said at least one respiratory parameter of said subject as a function of said first, second, third, fourth, fifth, sixth, seventh, eighth and ninth AC magnetic field strength signals, said processing system being further programmed and configured to determine a sleep disorder of said subject as a function of said at least one respiratory parameter and said at least one respiratory parameter value;

(ii) positioning said respiratory parameter monitoring system on a first subject;

(iii) initiating said respiratory parameter monitoring system, wherein said first AC magnetic field is generated and transmitted in said first, second and third dimensions by said permanent magnet;

(iv) detecting and measuring said first, fourth and seventh variable field strengths in said first, second and third field dimensions of said first AC magnetic field with said first magnetometer;

(v) detecting and measuring said second, fifth and eighth variable field strengths in said first, second and third field dimensions of said first AC magnetic field with said second magnetometer;

(vi) detecting and measuring said second, fifth and eighth variable field strengths in said first, second and third field dimensions of said first AC magnetic field with said third magnetometer;

(vii) generating said first, second and third AC magnetic field strength signals with said first magnetometer;

(viii) generating said fourth, fifth and sixth AC magnetic field strength signals with said second magnetometer;

(ix) generating said seventh, eighth and ninth AC magnetic field strength signals with said third magnetometer;

(x) transmitting said first, second and third AC magnetic field strength signals to said electronics module with said first magnetometer;

(xi) transmitting said fourth, fifth and sixth AC magnetic field strength signals to said electronics module with said second magnetometer;

(xii) transmitting said seventh, eighth and ninth AC magnetic field strength signals to said electronics module with said third magnetometer;

(xiii) determining at least one anatomical displacement of said first subject as a function of said first, second, third, fourth, fifth, sixth, seventh, eighth and ninth AC magnetic field strength signals with said electronics module;

(xiv) determining at least one respiratory parameter as a function of said at least one anatomical displacement with said electronics module;

(xv) determining a respiratory parameter value for said respiratory parameter as a function of said first, second, third, fourth, fifth, sixth, seventh, eighth and ninth AC magnetic field strength signals with said electronics module; and (xvi) determining a first sleep disorder of said first subject as a function of said determined at least one respiratory parameter and said determined value thereof with said electronics module.

20. The method of claim 19, wherein said first sleep disorder of said first subject comprises an apnea.

21. The method of claim 19, wherein prior to said step of providing said wearable garment said method includes the step of pre-measuring a first baseline respiratory parameter of said first subject to determine a first baseline respiratory parameter value of said first subject.

22. The method of claim 21, wherein said first sleep disorder of said first subject is determined as a function of said first baseline respiratory parameter value and said determined at least one respiratory parameter and said determined value thereof.

23. The method of claim 19, wherein said wearable garment further comprises a physiological parameter monitoring sub-system, and wherein prior to said step of providing said wearable garment said method includes the steps of pre-measuring a second baseline respiratory parameter of said first subject to determine a second baseline respiratory parameter value of said first subject, and measuring a first physiological parameter of said first subject to determine a first physiological parameter value of said first subject.

24. The method of claim 23, wherein said first sleep disorder of said first subject is determined as a function of said second baseline respiratory parameter value of said first subject, said first physiological parameter value of said first subject, and said determined at least one respiratory parameter and said determined value thereof.

25. The method of claim 23, wherein prior to said step of providing said wearable garment said method further includes the step of acquiring baseline accelerometer data of said first subject to establish the initial resting position parameters of said first subject.

26. The method of claim 25, wherein said first sleep disorder of said first subject is determined as a function of said baseline accelerometer data, second baseline respiratory parameter value, said first physiological parameter value, and said determined at least one respiratory parameter and said determined value thereof.

27. The method of claim 19, wherein said processing system is further programmed and configured to generate a diagnostic data set comprising an array of determined minute ventilation values and anatomical displacements of said first subject that are measured at defined anatomical points of said first subject, determine at least one apneic event as a function of said diagnostic data set, and determine said sleep disorder as a function of said at least one apneic event.

* * * * *